United States Patent
Shibata

(10) Patent No.: US 12,180,432 B2
(45) Date of Patent: Dec. 31, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventor: Natsumi Shibata, Tokyo (JP)

(73) Assignee: Resonac Corporation, Tokyo (JP)

( * ) Notice: Subject to any disclaimer, the term of this patent is extended or adjusted under 35 U.S.C. 154(b) by 0 days.

(21) Appl. No.: 18/020,821

(22) PCT Filed: Aug. 11, 2021

(86) PCT No.: PCT/JP2021/029599
§ 371 (c)(1),
(2) Date: Feb. 10, 2023

(87) PCT Pub. No.: WO2022/039079
PCT Pub. Date: Feb. 24, 2022

(65) Prior Publication Data
US 2023/0287288 A1    Sep. 14, 2023

(30) Foreign Application Priority Data
Aug. 20, 2020  (JP) .................. 2020-139604

(51) Int. Cl.
*C10M 107/38*   (2006.01)
*C10N 20/04*    (2006.01)
(Continued)

(52) U.S. Cl.
CPC ......... *C10M 107/38* (2013.01); *G11B 5/7257* (2020.08); *C10N 2020/04* (2013.01);
(Continued)

(58) Field of Classification Search
CPC ............... C10M 107/38; G11B 5/7257; C10N 2020/04; C10N 2030/06; C10N 2030/08; C10N 2040/18
See application file for complete search history.

(56) References Cited

U.S. PATENT DOCUMENTS

| | | | |
|---|---|---|---|
| 11,180,457 B2 * | 11/2021 | Kato | ........ C10M 107/46 |
| 2012/0008228 A1 * | 1/2012 | Mabuchi | ........ G11B 5/7257 |
| | | | 548/252 |
| 2019/0084911 A1 * | 3/2019 | Yagyu | .......... C07D 277/24 |

FOREIGN PATENT DOCUMENTS

| JP | 62-057418 A | 3/1987 |
|---|---|---|
| JP | 11-131083 A | 5/1999 |

(Continued)

*Primary Examiner* — Holly Rickman
(74) *Attorney, Agent, or Firm* — Sughrue Mion, PLLC

(57) ABSTRACT

A fluorine-containing ether compound represented by Formula (1) is provided.

$$R^1\!-\!O\!-\!R^2\!-\!CH_2\!-\!R^3\!-\!CH_2\!-\!R^4\!-\!R^5 \quad (1)$$

(in the formula, $R^3$ is a perfluoropolyether chain; $R^1$ is an alkenyl group having 2 to 8 carbon atoms or an alkynyl group having 3 to 8 carbon atoms; $R^2$ and $R^4$ are each independently a divalent linking group having one or more hydroxyl groups; and —$R^5$ is a group represented by Formula (2) shown below.)

$$-\!O\!-\!(CH_2)_g\!-\!N\!-\!R^6R^7 \quad (2)$$

(in the formula, g is an integer of 2 or 3; $R^6$ and $R^7$ are the same or different saturated aliphatic groups; and $R^6$ and $R^7$ may form a ring structure together with a nitrogen atom.)

13 Claims, 1 Drawing Sheet

(51) Int. Cl.
*C10N 30/06* (2006.01)
*C10N 30/08* (2006.01)
*C10N 40/18* (2006.01)
*G11B 5/725* (2006.01)

(52) U.S. Cl.
CPC ...... *C10N 2030/06* (2013.01); *C10N 2030/08* (2013.01); *C10N 2040/18* (2013.01)

(56) References Cited

FOREIGN PATENT DOCUMENTS

| | | |
|---|---|---|
| JP | 2006-225572 A | 8/2006 |
| JP | 4099860 B2 | 6/2008 |
| JP | 2019-067468 A | 4/2019 |
| WO | 2019/054148 A1 | 3/2019 |
| WO | 2019/087548 A1 | 5/2019 |

* cited by examiner

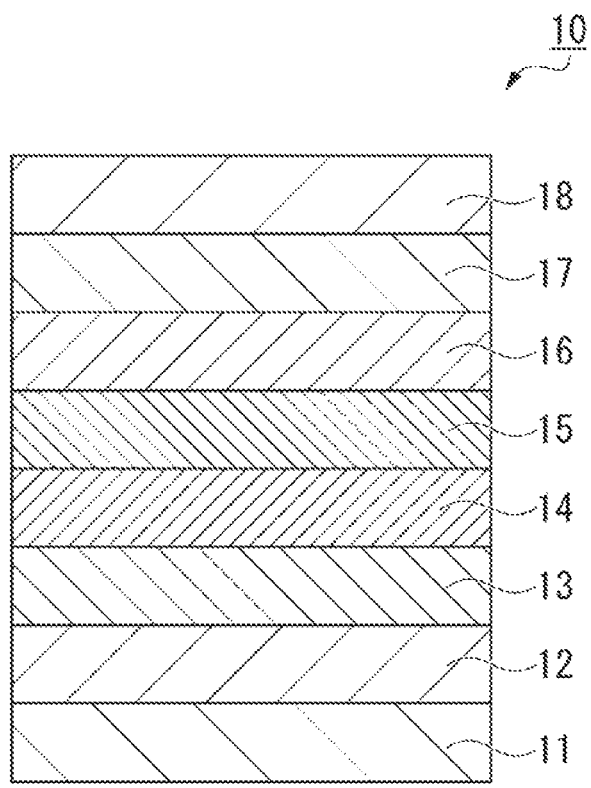

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2021/029599 filed Aug. 11, 2021, claiming priority based on Japanese Patent Application No. 2020-139604 filed Aug. 20, 2020, the content of which is incorporated herein by reference.

TECHNICAL FIELD

The present invention relates to a fluorine-containing ether compound, a lubricant for a magnetic recording medium, and a magnetic recording medium.

BACKGROUND ART

Development of magnetic recording media suitable for high recording densities is underway to increase the recording densities of magnetic recording and reproducing devices.

As a conventional magnetic recording medium, there has been a magnetic recording medium in which a recording layer is formed on a substrate and a protective layer made of carbon or the like is furthermore formed on the recording layer. The protective layer protects information recorded in the recording layer and enhances the slidability of a magnetic head.

However, sufficient durability of the magnetic recording medium cannot be obtained by simply providing the protective layer on the recording layer. Therefore, it is common to apply a lubricant to the surface of the protective layer to form a lubricating layer.

As a lubricant that is used at the time of forming a lubricating layer in a magnetic recording medium, for example, a lubricant containing a compound having a polar group such as a hydroxy group or an amino group at a terminal of a fluorine-based polymer having a repeating structure containing $CF_2$ has been proposed.

For example, Patent Document 1 discloses a fluoropolyether compound having an amino alcohol group at a molecular terminal. In addition, Patent Document 2 discloses a fluorine-containing ether compound in which an alkenyl group or alkynyl group bonds to one terminal of a perfluoropolyether chain and a group containing a heterocyclic ring bonds to the other terminal of the perfluoropolyether chain. In addition, Patent Document 3 discloses a fluoroether compound having amine groups having a hydroxyl group at both molecular terminals thereof. In addition, Patent Document 4 discloses a perfluoropolyether-based liquid lubricant having an amine-based functional group in at least one terminal of a chain-like molecule.

CITATION LIST

Patent Document

Patent Document 1: Japanese Unexamined Patent Application, First Publication No. H11-131083
Patent Document 2: PCT International Publication No. WO2019/087548
Patent Document 3: Japanese Unexamined Patent Application, First Publication No. 2006-225572
Patent Document 4: Japanese Patent No. 4099860
Patent Document 5: Japanese Unexamined Patent Application, First Publication No. S62-57418
Patent Document 6: Japanese Unexamined Patent Application, First Publication No. 2019-67468
Patent Document 7: PCT International Publication No. WO2019/054148

SUMMARY OF INVENTION

Technical Problem

There is a demand for a further decrease in the flying height of a magnetic head in magnetic recording and reproducing devices. Accordingly, a further decrease in the thickness of lubricating layers in magnetic recording media is required.

However, usually, there is a tendency that a decrease in the thickness of lubricating layers degrades the coatability of the lubricating layers and thereby degrades the wear resistance of magnetic recording media. In addition, conventional lubricating layers have insufficient heat resistance, and there has been a demand for improved heat resistance.

The present invention has been made in consideration of the above-described circumstances, and an object of the present invention is to provide a suitable fluorine-containing ether compound as a material for a lubricant for a magnetic recording medium which is capable of forming lubricating layers having excellent wear resistance and heat resistance.

In addition, another object of the present invention is to provide a lubricant for a magnetic recording medium that contains the fluorine-containing ether compound of the present invention and that is capable of forming lubricating layers having excellent wear resistance and heat resistance.

In addition, still another object of the present invention is to provide a magnetic recording medium having excellent wear resistance and heat resistance in which a lubricating layer containing the fluorine-containing ether compound of the present invention is provided and the thickness of the lubricating layer can be reduced.

Solution to Problem

A first aspect of the present invention provides the following fluorine-containing ether compound.

[1] A fluorine-containing ether compound represented by Formula (1) shown below.

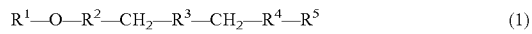
$$R^1-O-R^2-CH_2-R^3-CH_2-R^4-R^5 \quad (1)$$

(in Formula (1), $R^3$ is a perfluoropolyether chain; $R^1$ is an alkenyl group having 2 to 8 carbon atoms or an alkynyl group having 3 to 8 carbon atoms; $R^2$ and $R^4$ are each independently a divalent linking group having one or more hydroxyl groups; and $-R^5$ is a group represented by Formula (2) shown below.)

$$-O-(CH_2)_g-N-R^6R^7 \quad (2)$$

(in Formula (2), g is an integer of 2 or 3; $R^6$ and $R^7$ are the same or different saturated aliphatic groups; and $R^6$ and $R^7$ may form a ring structure together with a nitrogen atom.)

The compound of the first aspect of the present invention preferably has characteristics described in [2] to [11] below. Combinations of two or more of these characteristics are also preferable.

[2] The fluorine-containing ether compound according to [1], in which —$R^2$— in Formula (1) is represented by Formula (3) shown below.

(in Formula (3), a represents an integer of 1 to 3, and z represents 0 or 1; [X] is represented by Formula (X) shown below, [Y] is represented by Formula (Y) shown below, and a bonding order of [X] and [Y] may be reversed; and a sum of c in Formula (X) and e in Formula (Y) is 1 or 2.)

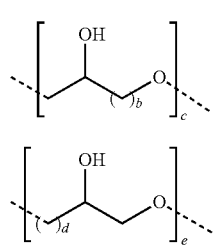

(in Formula (X), b is an integer of 1 to 3, and c is an integer of 0 to 2.)
(in Formula (Y), d is an integer of 2 or 3, and e is an integer of 0 to 2.)

[3] The fluorine-containing ether compound according to [1] or [2], in which —$R^4$— in Formula (1) is represented by Formula (4) shown below.

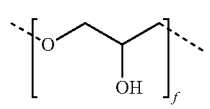

(in Formula (4), f is an integer of 1 or 2.)

[4] The fluorine-containing ether compound according to any one of [1] to [3], in which a total number of hydroxyl groups contained in $R^2$ and hydroxyl groups contained in $R^4$ is 3 or more.

[5] The fluorine-containing ether compound according to any one of [1] to [4], in which $R^6$ and $R^7$ in Formula (2) are each independently a saturated aliphatic group having 1 to 4 carbon atoms, or $R^6$ and $R^7$ form a 5- to 7-membered ring together with a nitrogen atom.

[6] The fluorine-containing ether compound according to any one of [1] to [4], in which —N—$R^6R^7$ in Formula (2) is a dimethylamino group or a diethylamino group.

[7] The fluorine-containing ether compound according to any one of [1] to [4], in which —N—$R^6R^7$ in Formula (2) is any one group selected from a pyrrolidine group, a piperidine group, a morpholine group, and a hexamethyleneimine group.

[8] The fluorine-containing ether compound according to any one of [1] to [7], in which $R^1$ in Formula (1) is any one group selected from a vinyl group, an allyl group, a 3-butenyl group, a 4-pentenyl group, and a propargyl group.

[9] The fluorine-containing ether compound according to any one of [1] to [8], in which $R^3$ is any of Formulae (5) to (7) shown below.

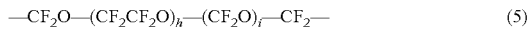

(each of h and i in Formula (5) indicates an average degree of polymerization and represents 0 to 30, provided that h and i are not both 0.)

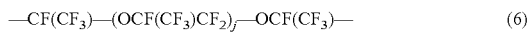

(j in Formula (6) indicates an average degree of polymerization and represents 0.1 to 30.)

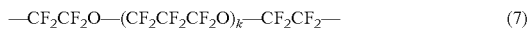

(k in Formula (7) indicates an average degree of polymerization and represents 0.1 to 30.)

[10] The fluorine-containing ether compound according to any one of [1] to [9], in which a number-average molecular weight thereof is within a range of 500 to 10,000.

[11] The fluorine-containing ether compound according to [1], in which the compound represented by Formula (1) is any of compounds represented by Formulae (A), (B), (E), (F), and (I) shown below.

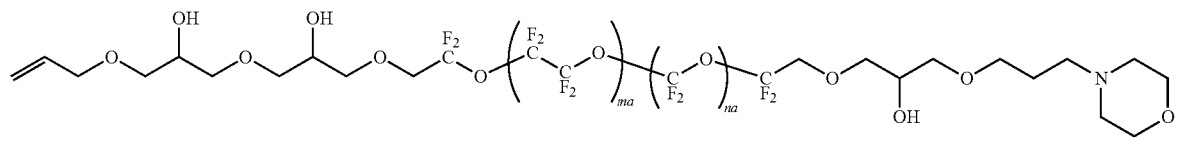

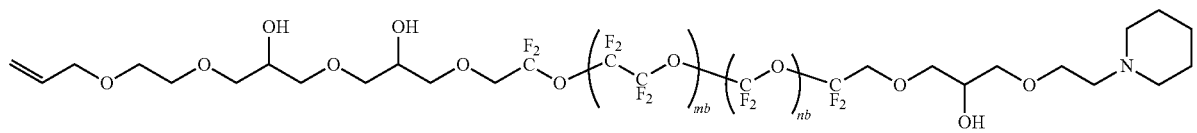

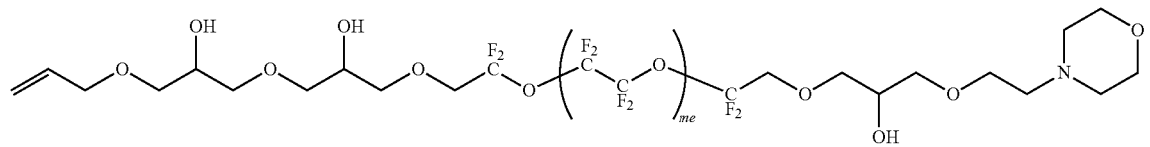

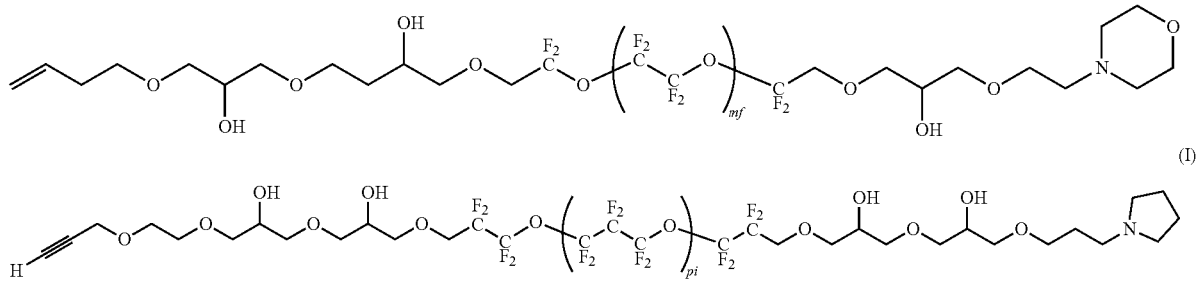

(in Formula (A), ma and na indicate average degrees of polymerization, where ma represents 1 to 30, and na represents 0 to 30.)
(in Formula (B), mb and nb indicate average degrees of polymerization, where mb represents 1 to 30, and nb represents 0 to 30.)
(in Formula (E), me indicates an average degree of polymerization, where me represents 0.1 to 30.)
(in Formula (F), mf indicates an average degree of polymerization, where mf represents 0.1 to 30.)
(in Formula (I), pi indicates an average degree of polymerization, where pi represents 0.1 to 30.)

A second aspect of the present invention provides the following lubricant.

[12] A lubricant for a magnetic recording medium, in which the lubricant contains the fluorine-containing ether compound according to any one of [1] to [11].

A third aspect of the present invention provides the following magnetic recording medium.

[13] A magnetic recording medium including, on a substrate, at least: a magnetic layer; a protective layer; and a lubricating layer, in this order, in which the lubricating layer contains the fluorine-containing ether compound according to any one of [1] to [11].

[14] The magnetic recording medium according to [13], in which an average film thickness of the lubricating layer is 0.5 nm to 2.0 nm.

Advantageous Effects of Invention

The fluorine-containing ether compound of the present invention is the compound represented by Formula (1) shown above and thus is suitable as a material for the lubricant for a magnetic recording medium.

The lubricant for a magnetic recording medium of the present invention contains the fluorine-containing ether compound of the present invention and thus can form a lubricating layer having excellent wear resistance and heat resistance.

The magnetic recording medium of the present invention includes the lubricating layer having excellent wear resistance and heat resistance and thus can reduce the thickness of the lubricating layer, resulting in excellent reliability and durability.

BRIEF DESCRIPTION OF DRAWINGS

The FIGURE is a schematic cross-sectional view showing a preferable embodiment of a magnetic recording medium of the present invention.

DESCRIPTION OF EMBODIMENTS

The inventors of the present invention repeated intensive studies as described below to achieve the above-described objects.

As a result, it was found that a compound having an alkenyl group or alkynyl group at a terminal of a perfluoropolyether chain is capable of forming a lubricating layer having excellent wear resistance. However, the heat resistance of the lubricating layer formed using this compound was insufficient. The reason for this is presumed to be because compounds having an alkenyl group or alkynyl group are likely to be oxidized under heating treatment conditions. More specifically, when the alkenyl group and/or the alkynyl group in the lubricating layer is oxidized under heating treatment conditions, oxidative decomposition products are generated. The generated oxidative decomposition products cannot stay on a magnetic recording medium rotating at high speed in a hard disk drive. Therefore, it is presumed that the high-speed rotation of a magnetic recording medium degrades the coatability of the lubricating layer, and thereby the wear resistance of the magnetic recording medium deteriorates.

In this respect, the inventors of the present invention made further examinations to inhibit the thermal decomposition of an alkenyl group or alkynyl group contained in a fluorine-containing ether compound.

As a result, it was found that a fluorine-containing ether compound in which a first terminal of a perfluoropolyether chain is an alkenyl group or alkynyl group and a second terminal is a tertiary amine group linked to two or three methylene groups, is sufficient. In addition, it was also confirmed that excellent heat resistance is obtained in such a fluorine-containing ether compound because the tertiary amine inhibits the thermal decomposition of the alkenyl group or alkynyl group. Furthermore, it was confirmed that excellent wear resistance can be obtained in a lubricating layer containing this fluorine-containing ether compound, and thereby the present invention was conceived.

Hereinafter, preferable examples of a fluorine-containing ether compound, a lubricant for a magnetic recording medium (hereinafter, abbreviated as "lubricant" in some cases), and a magnetic recording medium of the present invention will be described in detail. The present invention is not limited only to an embodiment to be described below. For example, the present invention is not limited only to the following examples, and additions, omissions, substitutions, and changes can be made regarding numbers, amounts, ratios, compositions, types, positions, materials, configurations, and the like within a range not departing from the scope of the present invention.

[Fluorine-Containing Ether Compound]

A fluorine-containing ether compound of the present embodiment is represented by Formula (1).

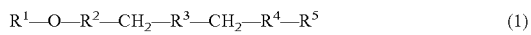

$$R^1-O-R^2-CH_2-R^3-CH_2-R^4-R^5 \qquad (1)$$

(in Formula (1), $R^3$ is a perfluoropolyether chain; $R^1$ is an alkenyl group having 2 to 8 carbon atoms or an alkynyl group having 3 to 8 carbon atoms; $R^2$ and $R^4$ are each independently a divalent linking group having one or more hydroxyl groups; and $-R^5$ is a group represented by Formula (2).)

$$-O-(CH_2)_g-N-R^6R^7 \qquad (2)$$

(in Formula (2), g is an integer of 2 or 3; $R^6$ and $R^7$ are the same or different saturated aliphatic groups; and $R^6$ and $R^7$ may form a ring structure together with a nitrogen atom.)

(Alkenyl Group or Alkynyl Group Represented by $R^1$)

In the fluorine-containing ether compound represented by Formula (1) shown above, $R^1$ is an alkenyl group having 2 to 8 carbon atoms or an alkynyl group having 3 to 8 carbon atoms. In the fluorine-containing ether compound of the present embodiment, the alkenyl group or alkynyl group of $R^1$ and the hydroxyl group (—OH) of $R^2$ exhibit favorable interaction with a protective layer in a lubricating layer containing these groups. In the fluorine-containing ether compound of the present embodiment, the alkenyl group having 2 to 8 carbon atoms as $R^1$ or the alkynyl group having 3 to 8 carbon atoms as $R^1$ can be appropriately selected depending on performance and the like required for lubricants containing the fluorine-containing ether compound.

When $R^1$ is an alkenyl group having 2 to 8 carbon atoms, $R^1$ is a group having one carbon-carbon double bond. In a case where $R^1$ is an alkenyl group, when the number of carbon atoms in the alkenyl group is 8 or less, the distance between the double bond of $R^1$ and the hydroxyl group of $R^2$ is appropriate regardless of what structure the alkenyl group has. Accordingly, the fluorine-containing ether compound represented by Formula (1) exhibits favorable interaction with a protective layer in a lubricating layer containing the fluorine-containing ether compound.

The alkenyl group having 2 to 8 carbon atoms as $R^1$ is not particularly limited, and examples thereof include a vinyl group, an allyl group, a crotyl group, a butenyl group, a betamethallyl group, a methylbutenyl group, a pentenyl group, a hexenyl group, a heptenyl group, and an octenyl group. Among these, an alkenyl group having 2 to 5 carbon atoms is preferable because then a lubricating layer exhibiting favorable affinity for a protective layer of a magnetic recording medium can be obtained. Specifically, a vinyl group, an allyl group, a 3-butenyl group, and a 4-pentenyl group are preferable, and an allyl group and a 3-butenyl group are particularly preferable. When $R^1$ is an alkenyl group having 3 or more carbon atoms, a double bond is preferably disposed at a terminal end of the fluorine-containing ether compound, since this results in a fluorine-containing ether compound from which a lubricating layer exhibiting better interaction with a protective layer of a magnetic recording medium can be obtained.

When $R^1$ is an alkynyl group having 3 to 8 carbon atoms, $R^1$ is a group having one carbon-carbon triple bond. In a case where $R^1$ is an alkynyl group, when the number of carbon atoms in the alkynyl group is 8 or less, the distance between the triple bond of $R^1$ and the hydroxyl group of $R^2$ is appropriate regardless of what structure the alkynyl group has. Accordingly, the fluorine-containing ether compound represented by Formula (1) exhibits favorable interaction with a protective layer, when the fluorine-containing ether compound is contained in a lubricating layer.

The alkynyl group having 3 to 8 carbon atoms of $R^1$ is not particularly limited, and examples thereof include a 1-propynyl group, a propargyl group, a butynyl group, a methylbutynyl group, a pentynyl group, a methylpentynyl group, a hexynyl group, a methylhexynyl group, a heptynyl group, and an octynyl group. Among these, an alkynyl group having 3 to 5 carbon atoms is preferable because then a lubricating layer exhibiting favorable affinity for a protective layer of a magnetic recording medium can be obtained. Specifically, a 1-propynyl group, a propargyl group, a butynyl group, and a pentynyl group are preferable, and a propargyl group is particularly preferable. In addition, the alkynyl group may be in a form containing an alkenyl group in the molecule such as a vinylpentynyl group. When $R^1$ is an alkynyl group having 3 or more carbon atoms, it is preferable that a triple bond is disposed at the terminal end of the fluorine-containing ether compound, since a fluorine-containing ether compound from which a lubricating layer exhibiting better interaction with a protective layer of a magnetic recording medium can be obtained.

(Divalent Linking Group Represented by $R^2$)

$R^2$ in Formula (1) is a divalent linking group containing one or more hydroxyl groups. The number of hydroxyl groups contained in $R^2$ is preferably one or two. Since $R^2$ contains one or more hydroxyl groups, when a lubricating layer is formed on a protective layer using a lubricant containing the fluorine-containing ether compound of the present embodiment, the lubricating layer can be properly adhered to the protective layer. Therefore, the lubricating layer containing the fluorine-containing ether compound of the present embodiment has favorable affinity for the protective layer and has excellent wear resistance.

$-R^2-$ in Formula (1) is preferably represented by Formula (3).

$$-((CH_2)_a-O)_z-[X]-[Y]- \qquad (3)$$

(in Formula (3), a represents an integer of 1 to 3, and z represents 0 or 1; [X] is represented by Formula (X), [Y] is represented by Formula (Y), and a bonding order of [X] and [Y] may be reversed; and a sum of c in Formula (X) and e in Formula (Y) is 1 or 2.)

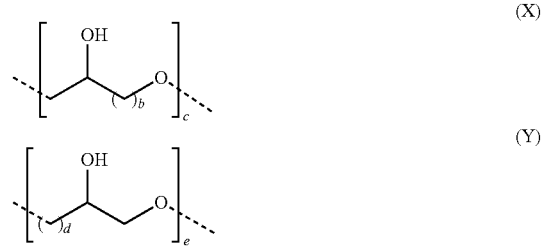

(in Formula (X), b is an integer of 1 to 3, and c is an integer of 0 to 2.)

(in Formula (Y), d is an integer of 2 or 3, and e is an integer of 0 to 2.)

a in Formula (3) is an integer of 1 to 3, and z is 0 or 1. When a and z are within these ranges, intramolecular aggregation of the alkenyl group or alkynyl group in $R^1$ and the hydroxyl group of (X) and/or (Y) can be prevented. Therefore, in a lubricating layer containing the fluorine-containing ether compound which is represented by Formula (1) and in which $-R^2-$ is represented by Formula (3), the alkenyl group or alkynyl group in $R^1$ and the hydroxyl group (—OH) in $R^2$ exhibit favorable interaction with a protective layer. Therefore, a lubricating layer having a high coating rate and having excellent wear resistance is obtained. In addition, since a in Formula (3) is an integer of 3 or less and z is 0 or 1, it is not difficult to obtain the adhesion of the alkenyl group or alkynyl group of $R^1$ and the hydroxyl group of $R^2$ to a protective layer, as chain structure in $R^2$ does not become too long and the mobility of the molecule does not increase by such a structure.

In Formula (3) shown above, b in Formula (X) is an integer of 1 to 3. When b is 3 or less, it is not difficult to obtain the adhesion of the alkenyl group or alkynyl group of $R^1$ and the hydroxyl group of $R^2$ to a protective layer, since a proportion of carbon atoms in the molecule does not become too high and the hydrophobicity of the molecule does not increase by such a proportion. In addition, since b in Formula (X) is an integer of 1 to 3, it is not difficult to obtain the adhesion of the hydroxyl group in Formula (X) to a protective layer, since molecular motion does not become excessive.

In addition, in a case where $R^2$ contains one hydroxyl group, when c in Formula (X) is 1 and b is an integer of 1 to 3, the hydroxyl group contained in $R^2$ is less likely to be affected by surrounding atoms, making the adhesion to a protective layer easy to obtain. In addition, in a case where $R^2$ contains two hydroxyl groups, when b is an integer of 1 to 3, the distance between the hydroxyl groups in $R^2$ is in an appropriate range (in which the number of atoms present between the two hydroxyl groups is 5 to 9), which makes it possible to prevent intramolecular aggregation.

In Formula (3) shown above, d in Formula (Y) is an integer of 2 or 3. When d is 3 or less, it is not difficult to obtain the adhesion of the alkenyl group or alkynyl group in $R^1$ and the hydroxyl group in $R^2$ to a protective layer, since a proportion of carbon atoms in the molecule is not too high and the hydrophobicity of the molecule does not increase by such a proportion. In addition, since d in Formula (Y) is an integer of 2 or 3, it is not difficult to obtain the adhesion of the hydroxyl group in Formula (Y) to a protective layer, since molecular motion does not become excessive.

In addition, in a case where $R^2$ contains one hydroxyl group, when e in Formula (Y) is 1 and d is an integer of 2 or 3, the hydroxyl group contained in $R^2$ is less likely to be affected by surrounding atoms, and the adhesion to a protective layer is easily obtained. In addition, in a case where $R^2$ contains two hydroxyl groups, when d is an integer of 2 or 3, the distance between the hydroxyl groups in $R^2$ is in an appropriate range (in which the number of atoms present between the two hydroxyl groups is 5 to 9), which makes it possible to prevent intramolecular aggregation.

In Formula (3) shown above, c in Formula (X) is an integer of 0 to 2, e in Formula (Y) is an integer of 0 to 2, and the sum of c and e is 1 or 2. Since c and e are within this range, when —$R^2$— is represented by Formula (3), $R^2$ has one or two hydroxyl groups. When the sum of c and e is 1 or more, in a case where a lubricating layer is formed on a protective layer using a lubricant containing the fluorine-containing ether compound of the present embodiment, the interaction between the hydroxyl group contained in $R^2$ and the protective layer can be obtained. When the sum of c and e is 2, the interaction between the hydroxyl group contained in $R^2$ and the protective layer becomes more significant.

In addition, since the sum of c and e in Formula (3) shown above is 2 or less, there is no case where the number of the hydroxyl groups contained in $R^2$ becomes too large, and thus, there is no case where the polarity of the fluorine-containing ether compound becomes excessively high. Therefore, it is possible to prevent the occurrence of pickup in which the fluorine-containing ether compound adheres to a magnetic head as foreign matter (smear).

(Divalent Linking Group Represented by $R^4$)

$R^4$ in Formula (1) is a divalent linking group containing one or more hydroxyl groups. The number of hydroxyl groups contained in $R^4$ is preferably one or two. Since $R^4$ contains one or more hydroxyl groups, when a lubricating layer is formed on a protective layer using a lubricant containing the fluorine-containing ether compound of the present embodiment, the lubricating layer can be properly adhered to a protective layer by the interaction between the hydroxyl groups contained in $R^4$ and the protective layer. Therefore, the lubricating layer containing the fluorine-containing ether compound of the present embodiment has favorable affinity for the protective layer and has excellent wear resistance.

—$R^4$— in Formula (1) is preferably represented by Formula (4).

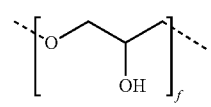

(in Formula (4), f is an integer of 1 or 2.)

In Formula (4), f is an integer of 1 or 2. Therefore, when $R^4$ is represented by Formula (4), $R^4$ has one or two hydroxyl groups. Since f is 2 or less, there is no case where the number of the hydroxyl groups in $R^4$ becomes too large, and thus, there is no case where the polarity of the fluorine-containing ether compound becomes excessively high. Therefore, it is possible to prevent the occurrence of pickup in which the fluorine-containing ether compound adheres to a magnetic head as foreign matter (smear).

$R^2$ and $R^4$ in Formula (1) are each independently a divalent linking group containing one or more hydroxyl groups. Therefore, the total number of hydroxyl groups contained in $R^2$ and $R^4$ is 2 or more. The total number of hydroxyl groups contained in $R^2$ and $R^4$ is preferably 3 or more, and more preferably 3 or 4. When the total number of hydroxyl groups contained in $R^2$ and $R^4$ is 3 or 4, a lubricating layer containing the fluorine-containing ether compound of the present embodiment easily obtains an appropriate adhesion to a protective layer.

(Group having tertiary amine represented by $R^5$ (Formula (2)))

—$R^5$ in Formula (1) is a group represented by Formula (2).

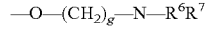

(g in Formula (2) is an integer of 2 or 3.)

The group represented by Formula (2) contains a tertiary amine (—N—$R^6R^7$). In a lubricating layer containing the fluorine-containing ether compound represented by Formula (1), an unshared electron pair of the nitrogen atom forming the tertiary amine exhibits a favorable interaction with a protective layer, thereby increasing the adhesion force with respect to the protective layer. In addition, the tertiary amine contained in the group represented by Formula (2) has a radical-scavenging function under heating treatment conditions. Accordingly, the fluorine-containing ether compound of the present embodiment has excellent heat resistance. In addition, a lubricating layer containing the fluorine-containing ether compound of the present embodiment, which has excellent heat resistance, can maintain an appropriate coating rate and has favorable wear resistance.

The nitrogen atom in the tertiary amine that is contained in $R^5$ bonds to an alkylene group ($-(CH_2)_g-$) in Formula (2). $-O-(CH_2)_g-$ in Formula (2) is a divalent linking group having an ether bond, and g in Formula (2) is an integer of 2 or 3. Accordingly, the fluorine-containing ether compound represented by Formula (1) has an appropriate distance between the nitrogen atom in the tertiary amine and the hydroxyl group ($-OH$) in $R^4$. Therefore, the fluorine-containing ether compound represented by Formula (1) is not prone to intramolecular aggregation and is easily disposed in a state of spreading and uniformly extending in a plane direction on a protective layer. Therefore, a lubricant containing the fluorine-containing ether compound represented by Formula (1) is capable of coating the surface of a protective layer at a high coating rate in spite of a thin thickness and is capable of forming a lubricating layer having excellent wear resistance.

On the other hand, when g in Formula (2) is less than 2, the fluorine-containing ether compound becomes prone to intramolecular aggregation. As a result, a lubricating layer containing this fluorine-containing ether compound is incapable of obtaining a sufficient coating rate when the thickness is made thin and is incapable of obtaining sufficient wear resistance. In addition, when g in Formula (2) exceeds 3, the alkylene group becomes too long, which increases the mobility of the molecular terminal, making the adhesion of the tertiary amine to a protective layer difficult to obtain.

In addition, in the fluorine-containing ether compound represented by Formula (1), since $R^4$ bonds to the group containing a tertiary amine ($-N-R^6R^7$) via an ether bond ($-O-$) in Formula (2), the molecular structure has an appropriate flexibility. Therefore, in a lubricating layer containing the fluorine-containing ether compound represented by Formula (1), the interaction between $R^4$ and a tertiary amine ($-N-R^6R^7$) in the fluorine-containing ether compound, and a protective layer disposed to be in contact with the lubricating layer becomes favorable. Accordingly, the lubricating layer containing the fluorine-containing ether compound is easily adsorbed to the protective layer, making the adhesion to the protective layer excellent and wear resistance excellent.

In the fluorine-containing ether compound represented by Formula (1), the structure of the tertiary amine contained in Formula (2) can be appropriately selected depending on performance and the like required for lubricants containing the fluorine-containing ether compound.

$R^6$ and $R^7$ in Formula (2) are the same or different saturated aliphatic groups. A saturated aliphatic group may be linear, branched, or cyclic. $R^6$ and $R^7$ may form a ring structure together with a nitrogen atom. The tertiary amine contained in Formula (2) is preferably a cyclic amine.

In a case where the tertiary amine contained in $R^5$ is an acyclic amine (where $R^6$ and $R^7$ do not form a ring structure together with a nitrogen atom), $R^6$ and $R^7$ are each preferably independently a saturated aliphatic group having 1 to 4 carbon atoms. In this case, the tertiary amine ($-N-R^6R^7$) in Formula (2) has an appropriate bulkiness, and thereby the fluorine-containing ether compound having an appropriate steric hindrance and an appropriate mobility is obtained. Therefore, in a lubricating layer containing this fluorine-containing ether compound, intramolecular aggregation due to the interaction between an unshared electron pair of the nitrogen atom of the tertiary amine contained in $R^5$, and the adjacent hydroxyl group can be prevented, making the adhesion with respect to a protective layer favorable. As a result, it is presumed that the coating rate of a protective layer can be maintained more appropriately, resulting in a lubricating layer having better wear resistance.

When $R^6$ and $R^7$ are each independently a saturated aliphatic group having 1 to 4 carbon atoms, examples of the saturated aliphatic group having 1 to 4 carbon atoms include a methyl group, an ethyl group, a normal propyl group, an isopropyl group, a normal butyl group, an isobutyl group, a sec-butyl group, and a tert-butyl group. Among these, saturated aliphatic groups having 1 or 2 carbon atoms are preferable. Specifically, $R^6$ and $R^7$ are each preferably independently a methyl group or an ethyl group, and $R^6$ and $R^7$ are more preferably the same. That is, in a case where the tertiary amine contained in $R^5$ is an acyclic amine, $-N-R^6R^7$ in Formula (2) is preferably any one group selected from a dimethylamino group, a methylethylamino group, and a diethylamino group, and is more preferably a dimethylamino group or a diethylamino group because these groups are easily synthesized.

In a case where the tertiary amine contained in $R^5$ is an acyclic amine (where $R^6$ and $R^7$ do not form a ring structure together with a nitrogen atom), specific examples of the tertiary amine ($-N-R^6R^7$) in Formula (2) include a dimethylamino group, a diethylamino group, a dipropylamino group, a diisopropylamino group, a di-normal-butylamino group, a diisobutylamino group, a di-sec-butylamino group, a di-tert-butylamino group, an ethylmethylamino group, a normal-propylmethylamino group, an isopropylmethylamino group, a normal-butylmethylamino group, an isobutylmethylamino group, a sec-butylmethylamino group, a tert-butylmethylamino group, an ethyl-normal-propylamino group, an ethyl isopropylamino group, an ethyl-normal-butylamino group, an ethyl isobutylamino group, a sec-butylethylamino group, a tert-butylethylamino group, an isopropylpropylamino group, a normal-butylpropylamino group, a (2-methylpropyl) (propyl) amino group, a N-sec-butylpropylamino group, a N-tert-butylpropylamino group, a N-(1-methylethyl)-1-butylamino group, a N-isopropyl-2-methyl-1-propylamino group, a N-(1-methylethyl)-2-butylamino group, a N-isopropyl-2-methyl-2-propylamino group, a butyl isobutylamino group, a butyl-sec-butylamino group, a butyl-tert-butylamino group, a N-(2-methylpropyl)-2-butylamino group, a N-(1,1-dimethylethyl)-2-methylpropylamino group, a N-(1,1-dimethylethyl)-2-butylamino group, and the like.

In a case where the tertiary amine contained in $R^5$ is a cyclic amine (where $R^6$ and $R^7$ form a ring structure together with a nitrogen atom), specific examples of the tertiary amine ($-N-R^6R^7$) in Formula (2) include an ethyleneimine group, an azacyclobutane group, a pyrrolidine group, a piperidine group, a morpholine group, a hexamethyleneimine group, a heptamethyleneimine group, an octamethyleneimine group, and the like.

In a case where the tertiary amine contained in $R^5$ is a cyclic amine (where $R^6$ and $R^7$ form a ring structure together with a nitrogen atom), the cyclic amine may have a substituent. Specific examples of the substituent include alkyl groups having a polar group and having 1 to 3 carbon atoms. In a case where the cyclic amine contained in $R^5$ has a substituent having a polar group, examples of the polar group include a hydroxyl group, an amino group, a carboxy group, and the like, among which a hydroxyl group is preferable. The bonding position of the substituent in the cyclic amine having a substituent is not particularly limited, and the substituent may bond to any of carbon atoms constituting the cyclic amine.

In a case where $R^6$ and $R^7$ form a ring structure together with a nitrogen atom, a heteroatom other than the nitrogen atom in the tertiary amine may be included in the ring structure. Examples of the heteroatom other than the nitrogen atom in the tertiary amine include an oxygen atom and/or a nitrogen atom.

In a case where the tertiary amine contained in $R^5$ is a cyclic amine, $R^6$ and $R^7$ preferably form a 5- to 7-membered ring together with the nitrogen atom. In this case, —N—$R^6R^7$ in Formula (2) has an appropriate bulkiness, and thereby the fluorine-containing ether compound having an appropriate steric hindrance and an appropriate mobility is obtained. As a result, a lubricating layer containing this fluorine-containing ether compound has a favorable affinity for a protective layer and excellent wear resistance. Specifically, —N—$R^6R^7$ in Formula (2) is preferably any one group selected from a pyrrolidine group, a piperidine group, a morpholine group, and a hexamethyleneimine group.

On the other hand, when the fluorine-containing ether compound represented by Formula (1) has, for example, a primary amine or a secondary amine instead of the tertiary amine in Formula (2), because primary amines or secondary amines have less steric hindrance than tertiary amines, an unshared electron pair of a nitrogen atom easily interacts with adjacent hydroxyl groups, which easily causes intramolecular aggregation. As a result, the coating rate of a lubricating layer containing this fluorine-containing ether compound is low, making wear resistance insufficient.

In addition, when the fluorine-containing ether compound represented by Formula (1) has an unsaturated heterocyclic ring containing a nitrogen atom instead of the tertiary amine in Formula (2), sufficient heat resistance cannot be obtained. This is because an unsaturated heterocyclic ring having a nitrogen atom itself is thermally decomposed under heating conditions. In addition, an unsaturated heterocyclic ring containing a nitrogen atom has less mobility as compared to tertiary amines. Therefore, in a lubricating layer containing this fluorine-containing ether compound, it is difficult for an unshared electron pair in the lubricating layer to approach a protective layer, making the adhesion to the protective layer difficult to obtain. Accordingly, wear resistance becomes insufficient.

(PFPE Chain Represented by $R^3$)

In the fluorine-containing ether compound represented by Formula (1), $R^3$ is a perfluoropolyether chain (hereinafter, abbreviated as "PFPE chain" in some cases). In a case of forming a lubricating layer by applying a lubricant containing the fluorine-containing ether compound of the present embodiment onto a protective layer, the PFPE chain coats the surface of the protective layer and also imparts lubricity to the lubricating layer to reduce a frictional force between a magnetic head and the protective layer.

The PFPE chain is appropriately selected depending on performance and the like required for lubricants containing the fluorine-containing ether compound. Examples of the PFPE chain include PFPE chains made of a perfluoromethylene oxide polymer, a perfluoroethylene oxide polymer, a perfluoro-n-propylene oxide polymer, a perfluoroisopropylene oxide polymer, a copolymer of monomers constituting these polymers, and the like.

The PFPE chain may be, for example, a structure represented by Formula (Rf) derived from a perfluoroalkylene oxide polymer or a copolymer.

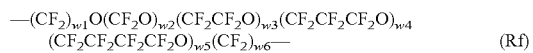
(Rf)

(in Formula (Rf), w2, w3, w4, and w5 each independently indicate an average degree of polymerization and represent 0 to 30, provided that w2, w3, w4, and w5 are not all 0 at the same time; w1 and w6 each independently indicate an average value indicating the number of —$CF_2$—'s and represent 1 to 3; and the arrangement order of the repeating units in Formula (Rf) is not particularly limited.)

In Formula (Rf), w2, w3, w4, and w5 each independently indicate an average degree of polymerization and represent 0 to 30, preferably 0 to 20, and more preferably 0 to 15.

In Formula (Rf), w1 and w6 each independently indicate an average value indicating the number of —$CF_2$—'s and represent 1 to 3. w1 and w6 are determined according to the structure of the repeating unit disposed at the end part of the chain structure in the polymer represented by Formula (Rf).

In Formula (Rf), ($CF_2O$), ($CF_2CF_2O$), ($CF_2CF_2CF_2O$), and ($CF_2CF_2CF_2CF_2O$) are repeating units. The arrangement order of the repeating units in Formula (Rf) is not particularly limited. In addition, the number of types of repeating units in Formula (Rf) is not particularly limited.

$R^3$ in Formula (1) is preferably, for example, a PFPE chain represented by Formula (Rf-1).

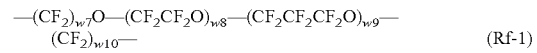
(Rf-1)

(in Formula (Rf-1), w8 and w9 each independently indicate an average degree of polymerization and represent 0.1 to 30; and w7 and w10 each independently indicate an average value indicating the number of —$CF_2$—'s and represent 1 to 2.)

The arrangement order of repeating units ($CF_2CF_2O$) and ($CF_2CF_2CF_2O$) in Formula (Rf-1) is not particularly limited. Formula (Rf-1) may include any of a random copolymer, a block copolymer, and an alternating copolymer which consist of monomer units ($CF_2CF_2O$) and ($CF_2CF_2CF_2O$). In Formula (Rf-1), w8 and w9, which indicate the average degree of polymerization, each independently represents 0.1 to 30, preferably 0.1 to 20, and more preferably 1 to 15. w7 and w10 in Formula (Rf-1) are each independently an average value indicating the number of —$CF_2$—'s and represent 1 to 2. w7 and w10 are determined according to the structure of the repeating unit disposed at the end part of the chain structure in the polymer represented by Formula (Rf-1).

$R^3$ in Formula (1) is also preferably represented by any of Formulae (5) to (7). In a case where $R^3$ is any of Formulae (5) to (7), the synthesis of the fluorine-containing ether compound is easy. In a case where $R^3$ is Formula (5) or (7), a raw material is readily available, which is more preferable.

In addition, in a case where $R^3$ is any of Formulae (5) to (7), the ratio of the number of oxygen atoms (the number of ether bonds (—O—)) to the number of carbon atoms in the perfluoropolyether chain is appropriate. Therefore, the fluorine-containing ether compound has an appropriate hardness. Accordingly, the fluorine-containing ether compound applied onto a protective layer is less likely to be aggregated on the protective layer, which makes it possible to form a lubricating layer having an even thinner thickness at a sufficient coating rate. In addition, in a case where $R^3$ is any of Formulae (5) to (7), this results in the fluorine-containing ether compound from which lubricating layers having favorable wear resistance can be obtained.

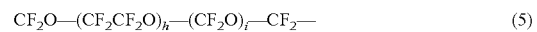
(5)

(each of h and i in Formula (5) indicates an average degree of polymerization and represents 0 to 30, provided that h and i are not both 0.)

In Formula (5), the arrangement order of (CF$_2$—CF$_2$—O) and (CF$_2$—O), which are repeating units, is not particularly limited. In Formula (5), the number h of (CF$_2$—CF$_2$—O)'s and the number i of (CF$_2$—O)'s may be the same or may be different from each other, provided that there is no case where h and i are both 0 at the same time. Formula (5) may include any of a random copolymer, a block copolymer, and an alternating copolymer which consist of monomer units (CF$_2$—CF$_2$—O) and (CF$_2$—O).

In Formula (5), h, which indicates the average degree of polymerization, is 0 to 30 and is preferably 1 to 20. Furthermore, h is preferably 3 to 10 because this results in the fluorine-containing ether compound from which a lubricating layer that easily wets and spreads on a protective layer and that has a uniform film thickness is easily obtained. For example, h is preferably 4 to 8 or 5 to 7. In Formula (5), i, which indicates the average degree of polymerization, is 0 to 30 and is preferably 1 to 20. Furthermore, i is preferably 3 to 10 because this results in the fluorine-containing ether compound from which a lubricating layer that easily wets and spreads on a protective layer and that has a uniform film thickness is easily obtained. For example, i is preferably 4 to 8 or 5 to 7.

—CF(CF$_3$)—(OCF(CF$_3$)CF$_2$)$_j$—OCF(CF$_3$)—   (6)

j in Formula (6) indicates an average degree of polymerization and represents 0.1 to 30.)

In Formula (6), j, which indicates the average degree of polymerization, is 0.1 to 30, preferably 1 to 30, and more preferably 2 to 20. Furthermore, j is further preferably 3 to 10 because this results in the fluorine-containing ether compound from which a lubricating layer that easily wets and spreads on a protective layer and that has a uniform film thickness is easily obtained. For example, j is preferably 4 to 8 or 5 to 7.

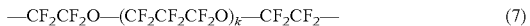

—CF$_2$CF$_2$O—(CF$_2$CF$_2$CF$_2$O)$_k$—CF$_2$CF$_2$—   (7)

(k in Formula (7) indicates an average degree of polymerization and represents 0.1 to 30.)

In Formula (7), k, which indicates the average degree of polymerization, is 0.1 to 30, preferably 1 to 30, and more preferably 2 to 20. Furthermore, k is further preferably 3 to 10 because this results in the fluorine-containing ether compound from which a lubricating layer that easily wets and spreads on a protective layer and that has a uniform film thickness is easily obtained. For example, k is preferably 4 to 8 or 5 to 7.

When h, i, j, and k which indicate the average degree of polymerization in Formulae (5) to (7) are each 30 or less, the viscosity of the fluorine-containing ether compound does not become too high, and lubricants containing this fluorine-containing ether compound become easy to apply, which is preferable.

The reason why a lubricating layer containing the fluorine-containing ether compound of the present embodiment has excellent heat resistance and wear resistance will be described.

In the fluorine-containing ether compound represented by Formula (1), the tertiary amine contained in R$^5$ inhibits the thermal decomposition of the alkenyl group or alkynyl group contained in R$^1$. Specifically, the tertiary amine contained in R$^5$ in the fluorine-containing ether compound contained in the lubricating layer scavenges radicals generated from oxygen in the atmosphere or oxygen present in the lubricating layer and/or on the protective layer under heating treatment conditions. As a result, the oxidative decomposition reaction due to radicals of the alkenyl group or alkynyl group contained in the fluorine-containing ether compound is inhibited. Therefore, in the lubricating layer containing the fluorine-containing ether compound represented by Formula (1), heat resistance is favorable, and the effect of improving wear resistance by the alkenyl group or alkynyl group contained in R$^1$ is maintained over a long period of time.

As a case of putting a lubricating layer under heating treatment conditions, for example, there are a case of performing a thermal treatment to heat a substrate on which the lubricating layer is formed to a temperature of, for example, 100° C. to 180° C., and a case of irradiating, with ultraviolet rays (UV), a substrate, on which the lubricating layer is formed, before the thermal treatment or after the thermal treatment, in order to improve the adhesion between the lubricating layer and a protective layer.

In general, the alkenyl group or alkynyl group in a fluorine-containing ether compound is susceptible to an oxidation reaction. Therefore, for example, when a lubricating layer containing a fluorine-containing ether compound that does not contain a tertiary amine but has an alkenyl group or alkynyl group is put under heating treatment conditions, the alkenyl group or alkynyl group is thermally decomposed, which generates an oxidative decomposition product.

The oxidative decomposition product generated by thermal decomposition of the alkenyl group or alkynyl group in the fluorine-containing ether compound is presumed to be a compound having aldehydes or ketones. This oxidative decomposition product is presumed to be generated when radicals, which have been generated from oxygen in the atmosphere or oxygen present in a lubricating layer and/or on a protective layer under heating treatment conditions, oxidize the α- and/or β-positions of the alkenyl group or alkynyl group in the lubricating layer.

The oxidative decomposition product generated by thermal decomposition is an unstable compound, and thus is thought to accelerate the oxidative decomposition of the alkenyl group or alkynyl group in the lubricating layer and to accelerate the deterioration of the lubricating layer. As a result, in the lubricating layer containing a fluorine-containing ether compound that does not contain a tertiary amine but has an alkenyl group or alkynyl group, it is presumed that the effect of improving wear resistance by the alkenyl group or alkynyl group in the lubricating layer is reduced in a short period of time.

Specifically, the fluorine-containing ether compound of the present embodiment is preferably compounds represented by Formulae (A) to (I). In Formulae (A) to (I), ma to mh, na to nd, and pi are values indicating the average degree of polymerization, and thus are not necessarily integers.

In all of the compounds represented by Formulae (A) to (H), R$^3$ in Formula (1) shown above is the PFPE chain represented by Formula (5) shown above, and R$^4$ is Formula (4) shown above. R$^2$ is Formula (3) shown above.

In the compound represented by Formula (A), R$^1$ in Formula (1) shown above is an allyl group, z in R$^2$ is 0, b is 1 and c is 2 in (X), e is 0 in (Y), g in Formula (2) is 3, and —N—R$^6$R$^7$ is a morpholine group.

In the compound represented by Formula (B), R$^1$ in Formula (1) shown above is an allyl group, a is 2 and z is 1 in R$^2$, b is 1 and c is 2 in (X), e is 0 in (Y), g in Formula (2) is 2, and —N—R$^6$R$^7$ is a piperidine group.

In the compound represented by Formula (C), R$^1$ in Formula (1) shown above is a propargyl group, a is 2 and z is 1 in R$^2$, b is 1 and c is 2 in (X), e is 0 in (Y), g in Formula (2) is 2, and —N—R$^6$R$^7$ is a pyrrolidine group.

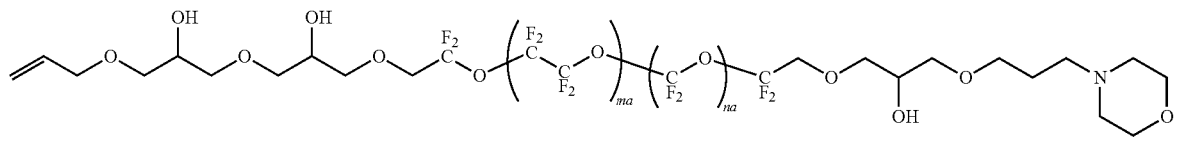

(A)

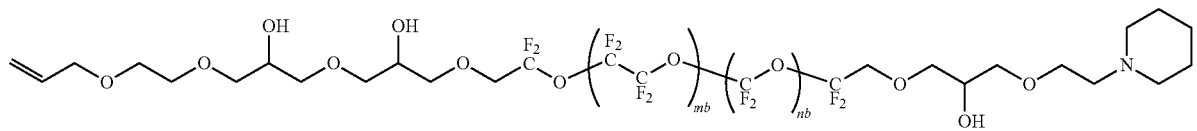

(B)

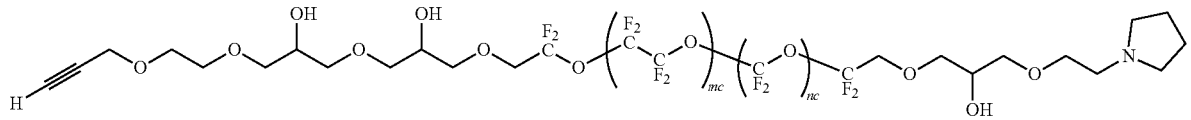

(C)

(in Formula (A), ma and na indicate average degrees of polymerization, where ma represents 1 to 30, and na represents 0 to 30.)

(in Formula (B), mb and nb indicate average degrees of polymerization, where mb represents 1 to 30, and nb represents 0 to 30.)

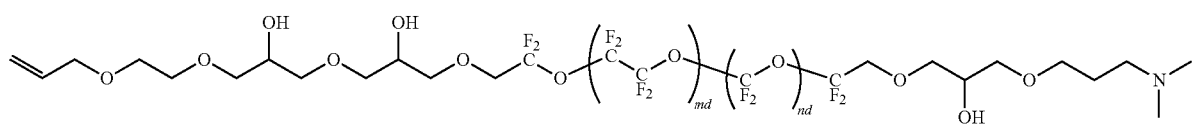

(D)

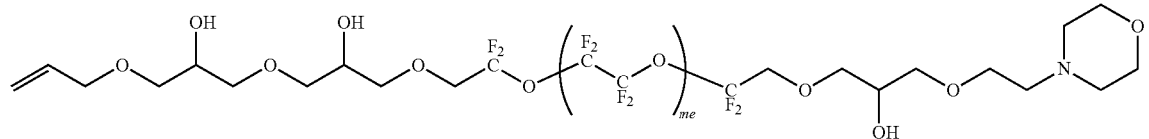

(E)

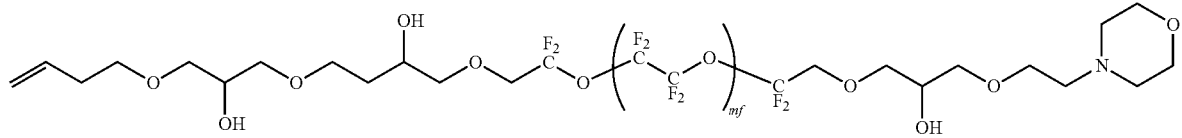

(F)

(in Formula (C), mc and nc indicate average degrees of polymerization, where me represents 1 to 30, and nc represents 0 to 30.)

The above-mentioned ma, mb, and me may be, for example, 1 to 20, 2 to 15, 3 to 10, 4 to 8, 5 to 7, and the like. The above-mentioned na, nb, and nc may be, for example, 0 to 25, 1 to 20, 2 to 15, 3 to 10, 4 to 8, 5 to 7, and the like.

In the compound represented by Formula (D), $R^1$ in Formula (1) shown above is an allyl group, a is 2 and z is 1 in $R^2$, b is 1 and c is 2 in (X), e is 0 in (Y), g in Formula (2) is 3, and —N—$R^6R^7$ is a dimethylamino group.

In the compound represented by Formula (E), $R^1$ in Formula (1) shown above is an allyl group, z in $R^2$ is 0, b is 1 and c is 2 in (X), e is 0 in (Y), g in Formula (2) is 2, and —N—$R^6R^7$ is a morpholine group.

In the compound represented by Formula (F), $R^1$ in Formula (1) shown above is a butenyl group, z in $R^2$ is 0, b is 1 and c is 1 in (X), d is 2 and e is 1 in (Y), g in Formula (2) is 2, and —N—$R^6R^7$ is a morpholine group.

(in Formula (D), md and nd indicate average degrees of polymerization, where md represents 1 to 30, and nd represents 0 to 30.)

(in Formula (E), me indicates an average degree of polymerization, where me represents 0.1 to 30.)

(in Formula (F), mf indicates an average degree of polymerization, where mf represents 0.1 to 30.)

The above-mentioned md may be, for example, 1 to 20, 2 to 15, 3 to 10, 4 to 8, 5 to 7, and the like. The above-mentioned nd may be, for example, 0 to 25, 1 to 20, 2 to 15, 3 to 10, 4 to 8, 5 to 7, and the like. The above-mentioned me and mf may be, for example, 0.1 to 25, 0.3 to 20, 0.5 to 15, 1 to 10, 2 to 8, 3 to 6, and the like.

In the compound represented by Formula (G), $R^1$ in Formula (1) shown above is a butenyl group, z in $R^2$ is 0, b is 1 and c is 1 in (X), d is 2 and e is 1 in (Y), g in Formula (2) is 2, and —N—$R^6R^7$ is a diethylamino group.

In the compound represented by Formula (H), $R^1$ in Formula (1) shown above is a pentenyl group, z in $R^2$ is 0, b is 1 and c is 2 in (X), e is 0 in (Y), g in Formula (2) is 2, and —N—$R^6R^7$ is a hexamethyleneimine group.

In the compound represented by Formula (I), $R^3$ in Formula (1) shown above is a PFPE chain represented by Formula (7), $R^4$ is Formula (4) shown above, $R^1$ is a propargyl group, a is 2 and z is 1 in $R^2$, b is 1 and c is 2 in (X), e is 0 in (Y), g in Formula (2) is 3, and —N—$R^6R^7$ is a pyrrolidine group.

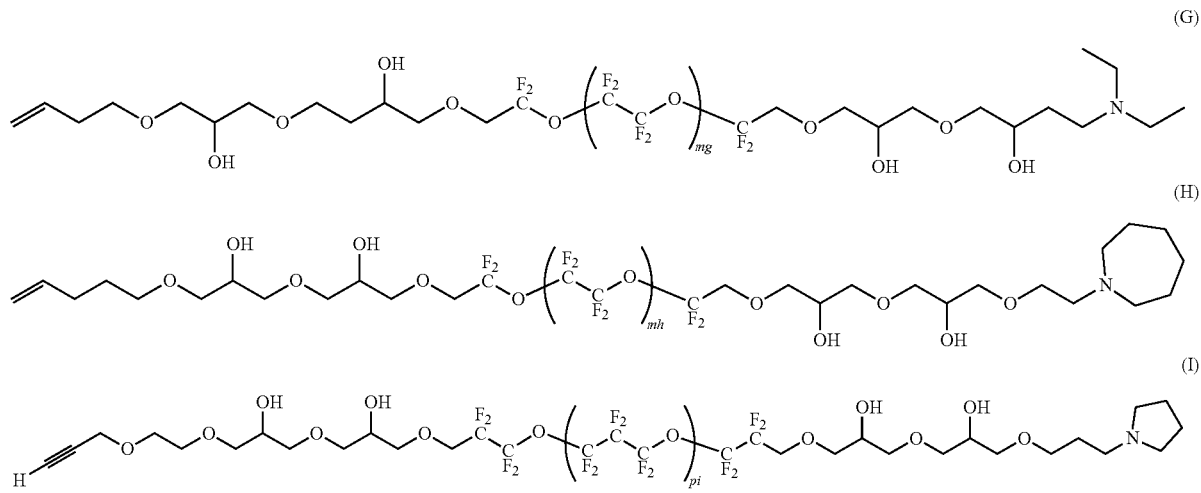

(in Formula (G), mg indicates an average degree of polymerization, where mg represents 0.1 to 30.)

(in Formula (H), mh indicates an average degree of polymerization, where mh represents 0.1 to 30.)

(in Formula (I), pi indicates an average degree of polymerization, where pi represents 0.1 to 30.)

The above-mentioned mg, mh, and pi may be, for example, 0.1 to 25, 0.3 to 20, 0.5 to 15, 1 to 10, 2 to 8, 3 to 6, and the like.

When the compound represented by Formula (1) is any one of the compounds represented by Formulae (A) to (I) shown above, raw materials are readily available. In addition, all of the compounds represented by Formulae (A) to (I) have excellent heat resistance. Furthermore, the compounds represented by Formulae (A) to (I) are capable of forming a lubricating layer having even better wear resistance and heat resistance in spite of a thin thickness. When the compound represented by Formula (1) is any one of the compounds represented by Formulae (A), (B), (E), (F), and (I), this is more preferable because then a lubricating layer having particularly excellent heat resistance can be formed.

The number-average molecular weight (Mn) of the fluorine-containing ether compound of the present embodiment is preferably within a range of 500 to 10,000, more preferably within a range of 700 to 7,000, and particularly preferably within a range of 1,000 to 3,000. When the number-average molecular weight is 500 or more, lubricants containing the fluorine-containing ether compound of the present embodiment are less likely to evaporate, which makes it possible to prevent the lubricants from evaporating and transferring to a magnetic head. In addition, when the number-average molecular weight is 10,000 or less, the viscosity of the fluorine-containing ether compound becomes appropriate, and by applying a lubricant containing this fluorine-containing ether compound, a lubricating layer having a thin thickness can be easily formed. When the number-average molecular weight is 3,000 or less, the viscosity becomes appropriate for handling in a case of applying to lubricants, which is preferable.

The number-average molecular weight (Mn) of the fluorine-containing ether compound is a value measured by $^1$H-NMR and $^{19}$F-NMR with AVANCE 111400 manufactured by Bruker BioSpin Group. In the nuclear magnetic resonance (NMR) measurement, a sample is diluted with a single or mixed solvent of hexafluorobenzene, acetone-d, tetrahydrofuran-d, and the like and is used in the measurement. As the reference of the $^{19}$F-NMR chemical shift, the peak of hexafluorobenzene is set to −164.7 ppm, and as the reference of the $^1$H-NMR chemical shift, the peak of acetone is set to 2.2 ppm.

"Production Method"

A method for producing the fluorine-containing ether compound of the present embodiment is not particularly limited, and the fluorine-containing ether compound can be produced using a well-known conventional production method. The fluorine-containing ether compound of the present embodiment can be produced using a production method described below, for example.

First, a fluorine-based compound having hydroxymethyl groups (—$CH_2OH$) each disposed at both terminals of a perfluoropolyether chain corresponding to $R^3$ in Formula (1) is prepared.

Next, the hydroxyl group in the hydroxymethyl group disposed at one terminal of the fluorine-based compound is substituted with a group composed of $R^1$—O—$R^2$— in Formula (1) (first reaction). Thereafter, the hydroxyl group in the hydroxymethyl group disposed at the other terminal is substituted with a group composed of —$R^4$-$R^5$ in Formula (1) (second reaction).

The first reaction and the second reaction can be performed using a well-known conventional method and can be appropriately determined depending on the types of $R^1$, $R^2$, $R^4$, and $R^5$ in Formula (1). In addition, among the first reaction and the second reaction, either reaction may be performed first.

The compound represented by Formula (1) is obtained by the above-described method.

In the present embodiment, for example, in the first reaction of introducing the group composed of $R^1$—O—$R^2$—, the hydroxyl group in the hydroxymethyl group at one terminal of the fluorine-based compound is preferably reacted with an epoxy compound corresponding to $R^1$—O—$R^2$—.

In addition, in the second reaction, in order to introduce the group composed of —$R^4$-$R^5$ into the fluorine-based compound, the hydroxyl group in the hydroxymethyl group at one terminal of the fluorine-based compound is preferably reacted with an epoxy compound corresponding to —$R^4$-$R^5$.

The epoxy compound used at the time of producing the fluorine-containing ether compound of the present embodiment can be synthesized by, for example, reacting an alcohol having a structure corresponding to the terminal group represented by $R^1$—O—$R^2$— or to the terminal group represented by —$R^4$-$R^5$ in the fluorine-containing ether compound to be produced with a compound having any epoxy group selected from epichlorohydrin, epibromohydrin, 2-bromoethyloxirane, and allyl glycidyl ether. Such an epoxy compound may be synthesized by a method of oxidizing an unsaturated bond, or a commercially available product may be purchased and used.

By forming a lubricating layer on a protective layer using a lubricant containing the fluorine-containing ether compound of the present embodiment, the effects described below can be obtained.

In the fluorine-containing ether compound represented by Formula (1), the alkenyl group or alkynyl group in $R^1$ exhibits favorable interaction with a protective layer. Accordingly, the lubricating layer containing the fluorine-containing ether compound represented by Formula (1) can maintain an appropriate coating rate on the protective layer, making wear resistance excellent.

In addition, when the tertiary amine contained in $R^5$ scavenges radicals, thermal decomposition of the alkenyl group or alkynyl group in $R^1$ is inhibited. Accordingly, the fluorine-containing ether compound represented by Formula (1) and the lubricating layer formed using the compound have favorable heat resistance. More specifically, the tertiary amine contained in $R^5$ scavenges radicals generated under heating treatment conditions such as a thermal treatment performed in the range of 100° C. to 180° C. Therefore, the oxidation reaction of the alkenyl group or alkynyl group in $R^1$ by radicals is inhibited, and thereby the effect of improving wear resistance by the alkenyl group or alkynyl group in $R^1$ is maintained.

Furthermore, since an unshared electron pair of the nitrogen atom forming the tertiary amine contained in $R^5$ exhibits favorable interaction with a protective layer, a lubricating layer having favorable adhesion force with respect to the protective layer is obtained. Therefore, the coating rate with respect to the protective layer can be appropriately maintained, making the wear resistance of the lubricating layer excellent.

In addition, the tertiary amine contained in $R^5$ has a moderate steric hindrance and mobility. Therefore, aggregation due to interaction with hydroxyl groups adjacent to the tertiary amine can be prevented without impairing the interaction with the protective layer by an unshared electron pair of the nitrogen atom forming the tertiary amine. As a result, the lubricating layer having an appropriate coating rate with respect to the protective layer and having excellent wear resistance is obtained.

The surface of the protective layer is coated with the PFPE chain represented by $R^3$ in the lubricating layer, and the frictional force between a magnetic head and the protective layer is reduced. Furthermore, the lubricating layer is adhered onto the protective layer by the bond between the protective layer and the hydroxyl group contained in $R^2$ linked to the first end portion of the PFPE chain represented by $R^3$ and by the bond between the protective layer and the hydroxyl group contained in $R^4$ linked to the second end portion of the PFPE chain. That is, in the fluorine-containing ether compound represented by Formula (1), since two or more hydroxyl groups are present at appropriate positions in the molecule, the interaction between the hydroxyl group and the protective layer is effectively obtained, and the surface of the protective layer is coated at a high coating rate. Therefore, the lubricating layer containing the fluorine-containing ether compound of the present embodiment is strongly bonded to the protective layer and has excellent wear resistance.

[Lubricant for Magnetic Recording Medium]

A lubricant for a magnetic recording medium of the present embodiment contains the fluorine-containing ether compound represented by Formula (1).

In the lubricant of the present embodiment, well-known materials that are used as materials for lubricants can be mixed and used as necessary as long as they are in a range not impairing characteristics attributed to incorporation of the fluorine-containing ether compound represented by Formula (1).

Specific examples of well-known materials include FOMBLIN (registered trademark) ZDIAC, FOMBLIN ZDEAL, FOMBLIN AM-2001 (all manufactured by Solvay Solexis), Moresco A20H (manufactured by Moresco Corporation), and the like. The number-average molecular weight of the well-known material that is used by being mixed with the lubricant of the present embodiment is preferably 1,000 to 10,000.

In a case where the lubricant of the present embodiment contains a material other than the fluorine-containing ether compound represented by Formula (1), the content of the fluorine-containing ether compound represented by Formula (1) in the lubricant of the present embodiment is preferably 50 mass % or more, and more preferably 70 mass % or more. The content of the fluorine-containing ether compound represented by Formula (1) may be 80 mass % or more, or may be 90 mass % or more. The upper limit value of the content can be arbitrarily selected, and may be 99 mass %, 97 mass %, or 95 mass %, for example.

The lubricant of the present embodiment contains the fluorine-containing ether compound represented by Formula (1) and is thus capable of coating the surface of a protective layer at a high coating rate in spite of a thin thickness, and thereby a lubricating layer having excellent adhesion to the protective layer and having excellent wear resistance and heat resistance can be formed.

[Magnetic Recording Medium]

A magnetic recording medium of the present embodiment includes at least a magnetic layer, a protective layer, and a lubricating layer which are sequentially provided on a substrate.

In the magnetic recording medium of the present embodiment, one or two or more underlayers can be provided as necessary between the substrate and the magnetic layer. In addition, it is also possible to provide an adhesive layer and/or a soft magnetic layer between the underlayer and the substrate.

The FIGURE is a schematic cross-sectional view showing an example of an embodiment of the magnetic recording medium of the present invention.

A magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

"Substrate"

As the substrate 11, for example, a non-magnetic substrate or the like in which a NiP or NiP alloy film is formed on a base made of a metal or alloy material such as Al or an Al alloy can be used.

In addition, as the substrate 11, a non-magnetic substrate made of a non-metal material such as glass, ceramic, silicon, silicon carbide, carbon, or resin may be used, and a non-magnetic substrate in which a NiP or NiP alloy film is formed on a base made of this non-metal material may also be used.

"Adhesive Layer"

The adhesive layer 12 prevents the progress of corrosion of the substrate 11 which may occur in a case where the substrate 11 and the soft magnetic layer 13, which is provided on the adhesive layer 12, are disposed in contact with each other.

The material of the adhesive layer 12 can be appropriately selected from, for example, Cr, a Cr alloy, Ti, a Ti alloy, CrTi, NiAl, an AlRu alloy, and the like. The adhesive layer 12 can be formed by, for example, a sputtering method.

"Soft Magnetic Layer"

The soft magnetic layer 13 preferably has a structure in which a first soft magnetic film, an interlayer made of a Ru film, and a second soft magnetic film are sequentially laminated. That is, the soft magnetic layer 13 preferably has a structure in which the interlayer made of a Ru film is sandwiched between the two soft magnetic films and thereby the soft magnetic films on and under the interlayer are antiferromagnetically coupled (AFC).

Examples of the material of the first soft magnetic film and the second soft magnetic film include a CoZrTa alloy, a CoFe alloy, and the like.

To the CoFe alloy that is used for the first soft magnetic film and the second soft magnetic film, any of Zr, Ta, and Nb is preferably added. This accelerates the amorphization of the first soft magnetic film and the second soft magnetic film, which makes it possible to improve the orientation of the first underlayer (seed layer) and makes it possible to reduce the flying height of a magnetic head.

The soft magnetic layer 13 can be formed by, for example, a sputtering method.

"First Underlayer"

The first underlayer 14 is a layer that controls the orientations and crystal sizes of the second underlayer 15 and the magnetic layer 16 which are provided on the first underlayer 14.

Examples of the first underlayer 14 include a Cr layer, a Ta layer, a Ru layer, a CrMo alloy layer, a CoW alloy layer, a CrW alloy layer, a CrV alloy layer, a CrTi alloy layer, and the like.

The first underlayer 14 can be formed by, for example, a sputtering method.

"Second Underlayer"

The second underlayer 15 is a layer that controls the orientation of the magnetic layer 16 to be favorable. The second underlayer 15 is preferably a Ru or Ru alloy layer.

The second underlayer 15 may be a layer formed of a single layer or may be composed of a plurality of layers. In a case where the second underlayer 15 is composed of a plurality of layers, all of the layers may be composed of the same material, or at least one layer may be composed of a different material.

The second underlayer 15 can be formed by, for example, a sputtering method.

"Magnetic Layer"

The magnetic layer 16 is made of a magnetic film in which the easy magnetization axis is directed in a perpendicular or horizontal direction with respect to the substrate surface. The magnetic layer 16 is a layer containing Co and Pt and may be a layer further containing an oxide or Cr, B, Cu, Ta, Zr, or the like in order to improve SNR characteristics.

Examples of the oxide that is contained in the magnetic layer 16 include $SiO_2$, SiO, $Cr_2O_3$, CoO, $Ta_2O_3$, $TiO_2$, and the like.

The magnetic layer 16 may be composed of a single layer or may be composed of a plurality of magnetic layers made of materials with different compositions.

For example, in a case where the magnetic layer 16 is composed of three layers of a first magnetic layer, a second magnetic layer, and a third magnetic layer which are sequentially laminated from below, the first magnetic layer is preferably a granular structure made of a material containing Co, Cr, and Pt and further containing an oxide. As the oxide that is contained in the first magnetic layer, for example, oxides of Cr, Si, Ta, Al, Ti, Mg, Co, or the like are preferably used. Among them, in particular, $TiO_2$, $Cr_2O_3$, $SiO_2$, and the like can be suitably used. In addition, the first magnetic layer is preferably made of a composite oxide to which two or more oxides have been added. Among them, in particular, $Cr_2O_3$—$SiO_2$, $Cr_2O_3$—$TiO_2$, $SiO_2$—$TiO_2$, and the like can be suitably used.

The first magnetic layer may contain, in addition to Co, Cr, Pt, and the oxide, one or more elements selected from B, Ta, Mo, Cu, Nd, W, Nb, Sm, Tb, Ru, and Re. For the second magnetic layer, the same material as for the first magnetic layer can be used. The second magnetic layer is preferably a granular structure.

The third magnetic layer is preferably a non-granular structure made of a material containing Co, Cr, and Pt but containing no oxides. The third magnetic layer may contain, in addition to Co, Cr, and Pt, one or more elements selected from B, Ta, Mo, Cu, Nd, W, Nb, Sm, Tb, Ru, Re, and Mn.

In a case where the magnetic layer 16 is formed of a plurality of magnetic layers, a non-magnetic layer is preferably provided between the magnetic layers adjacent to each other. In a case where the magnetic layer 16 is made up of three layers of the first magnetic layer, the second magnetic layer, and the third magnetic layer, it is preferable to provide a non-magnetic layer between the first magnetic layer and the second magnetic layer and between the second magnetic layer and the third magnetic layer.

For the non-magnetic layer that is provided between the magnetic layers adjacent to each other in the magnetic layer 16, it is possible to suitably use, for example, Ru, a Ru alloy, a CoCr alloy, a CoCrX1 alloy (where X1 represents one or two or more elements selected from Pt, Ta, Zr, Re, Ru, Cu, Nb, Ni, Mn, Ge, Si, O, N, W, Mo, Ti, V, and B), and the like.

For the non-magnetic layer that is provided between the magnetic layers adjacent to each other in the magnetic layer 16, an alloy material containing an oxide, a metallic nitride, or a metallic carbide is preferably used. Specifically, as the oxide, for example, $SiO_2$, $Al_2O_3$, $Ta_2O_5$, $Cr_2O_3$, MgO, $Y_2O_3$, $TiO_2$, and the like can be used. As the metallic nitride, for example, AlN, $Si_3N_4$, TaN, CrN, and the like can be used. As the metallic carbide, for example, TaC, BC, SiC, and the like can be used.

The non-magnetic layer can be formed by, for example, a sputtering method.

The magnetic layer 16 is preferably a magnetic layer for perpendicular magnetic recording in which the easy magnetization axis is directed in a direction perpendicular to the substrate surface in order to realize a higher recording density. The magnetic layer 16 may be a magnetic layer for longitudinal magnetic recording.

The magnetic layer 16 may be formed by any well-known conventional method such as a deposition method, an ion beam sputtering method, or a magnetron sputtering method. The magnetic layer 16 is normally formed by a sputtering method.

"Protective Layer"

The protective layer 17 protects the magnetic layer 16. The protective layer 17 may be composed of a single layer or may be composed of a plurality of layers. Examples of the material of the protective layer 17 include carbon, nitrogen-containing carbon, silicon carbide, and the like.

As the protective layer 17, a carbon-based protective layer can be preferably used, and, in particular, an amorphous carbon protective layer is preferable. When the protective layer 17 is a carbon-based protective layer, the interaction with the hydroxyl group that is included in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer is preferably 3 to 20 atomic % when measured by the hydrogen forward scattering method (HFS). In addition, the nitrogen content in the carbon-based protective layer is preferably 4 to 15 atomic % when measured by X-ray photoelectron spectroscopy (XPS).

The hydrogen and/or nitrogen that are contained in the carbon-based protective layer do not need to be uniformly contained throughout the entire carbon-based protective layer. For example, the carbon-based protective layer is suitably formed as a composition gradient layer in which nitrogen is contained in the lubricating layer 18 side of the protective layer 17 and hydrogen is contained in the magnetic layer 16 side of the protective layer 17. In this case, the adhesive force between the magnetic layer 16 and the carbon-based protective layer and between the lubricating layer 18 and the carbon-based protective layer is further improved.

The film thickness of the protective layer 17 may be set to 1 nm to 7 nm. When the film thickness of the protective layer 17 is 1 nm or more, performance of the protective layer 17 can be sufficiently obtained. The film thickness of the protective layer 17 is preferably 7 nm or less from the viewpoint of reducing the thickness of the protective layer 17.

As a method for forming the protective layer 17, it is possible to use a sputtering method in which a carbon-containing target material is used, a chemical vapor deposition (CVD) method in which a hydrocarbon raw material such as ethylene or toluene is used, an ion beam deposition (IBD) method, and the like.

In the case of forming a carbon-based protective layer as the protective layer 17, the carbon-based protective layer can be formed by, for example, a DC magnetron sputtering method. Particularly, in the case of forming a carbon-based protective layer as the protective layer 17, an amorphous carbon protective layer is preferably formed by a plasma CVD method. The amorphous carbon protective layer formed by the plasma CVD method has a uniform surface with small roughness.

"Lubricating layer"

The lubricating layer 18 prevents contamination of the magnetic recording medium 10. In addition, the lubricating layer 18 reduces a frictional force of a magnetic head of a magnetic recording and reproducing device, which slides on the magnetic recording medium 10, and thereby improves the durability of the magnetic recording medium 10.

The lubricating layer 18 is formed in contact with the protective layer 17 as shown in the FIGURE. The lubricating layer 18 contains the above-described fluorine-containing ether compound.

In a case where the protective layer 17, which is disposed below the lubricating layer 18, is a carbon-based protective layer, the lubricating layer 18 is bonded particularly to the protective layer 17 with a high bonding force. As a result, it becomes easy to obtain the magnetic recording medium 10 in which the surface of the protective layer 17 is coated with the lubricating layer 18 at a high coating rate in spite of a thin thickness, and it is possible to effectively prevent contamination on the surface of the magnetic recording medium 10.

The average film thickness of the lubricating layer 18 is preferably 0.5 nm (5 Å) to 2.0 nm (20 Å), and more preferably 0.5 nm (5 Å) to 1.0 nm (10 Å). When the average film thickness of the lubricating layer 18 is 0.5 nm or more, the lubricating layer 18 does not become an island shape or a mesh shape and is formed in a uniform film thickness. Therefore, the surface of the protective layer 17 can be coated with the lubricating layer 18 at a high coating rate. In addition, when the average film thickness of the lubricating layer 18 is set to 2.0 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes under the lubricating layer 18. The environmental substance that has intruded under the lubricating layer 18 is adsorbed and bonded to the protective layer 17 and generates a contamination substance. At the time of magnetic recording and reproducing, the generated contamination substance (aggregated component) adheres (transfers) to a magnetic head as a smear to break the magnetic head or degrade the magnetic recording and reproducing characteristics of magnetic recording and reproducing devices.

Examples of the environmental substance that generates the contamination substance include siloxane compounds (cyclic siloxane and linear siloxane), ionic impurities, hydrocarbons having a relatively high molecular weight such as octacosane, plasticizers such as dioctyl phthalate, and the like. Examples of a metal ion that is contained in the ionic impurities include a sodium ion, a potassium ion, and the like. Examples of an inorganic ion that is contained in the ionic impurities include a chlorine ion, a bromine ion, a nitrate ion, a sulfate ion, an ammonium ion, and the like. Examples of an organic ion that is contained in the ionic impurities include an oxalate ion, a formate ion, and the like.

"Method for Forming Lubricating Layer"

Examples of a method for forming the lubricating layer 18 include a method in which a magnetic recording medium that is not yet fully manufactured and thus includes the individual layers up to the protective layer 17 formed on the substrate 11 is prepared and a solution for forming the lubricating layer is applied on the protective layer 17 and dried.

The solution for forming the lubricating layer can be obtained by dispersing and dissolving the above-described lubricant for a magnetic recording medium of the embodiment in a solvent as necessary and setting the viscosity and concentration to be suitable for application methods.

Examples of the solvent that is used for the solution for forming the lubricating layer include fluorine-based solvents such as VERTREL (registered trademark) XF (trade name, manufactured by Dupont-Mitsui Fluorochemicals Co., Ltd.), and the like.

A method for applying the solution for forming the lubricating layer is not particularly limited, and examples thereof include a spin coating method, a spraying method, a paper coating method, a dipping method, and the like.

In the case of using the dipping method, it is possible to use, for example, a method to be described below. First, the substrate 11 on which the individual layers up to the protective layer 17 have been formed is immersed into the solution for forming the lubricating layer that has been put into an immersion vessel of a dip coater. Next, the substrate 11 is lifted from the immersion vessel at a predetermined speed. This applies the solution for forming the lubricating layer to the surface of the protective layer 17 located on the substrate 11.

The use of the dipping method makes it possible to uniformly apply the solution for forming the lubricating layer to the surface of the protective layer 17 and makes it possible to form the lubricating layer 18 on the protective layer 17 in a uniform film thickness.

In the present embodiment, a thermal treatment is preferably carried out on the substrate 11 on which the lubricating layer 18 has been formed. The thermal treatment improves the adhesion between the lubricating layer 18 and the protective layer 17 and improves the adhesive force between the lubricating layer 18 and the protective layer 17. The thermal treatment temperature is preferably set to 100° C. to 180° C. When the thermal treatment temperature is 100° C. or higher, an effect on improvement in the adhesion between the lubricating layer 18 and the protective layer 17 can be sufficiently obtained. In addition, when the thermal treatment temperature is set to 180° C. or lower, it is possible to prevent thermal decomposition of the lubricating layer 18. The thermal treatment time is preferably set to 10 to 120 minutes.

In the present embodiment, in order to further improve the adhesion force of the lubricating layer 18 to the protective layer 17, a treatment of irradiating the lubricating layer 18 located on the substrate 11 before the thermal treatment or after the thermal treatment with ultraviolet rays (UV) may be performed.

The magnetic recording medium 10 of the present embodiment has at least the magnetic layer 16, the protective layer 17, and the lubricating layer 18 which are sequentially provided on the substrate 11. In the magnetic recording medium 10 of the present embodiment, the lubricating layer 18 containing the above-described fluorine-containing ether compound is formed in contact with the protective layer 17. This lubricating layer 18 coats the surface of the protective layer 17 at a high coating rate in spite of a thin thickness. Therefore, in the magnetic recording medium 10 of the present embodiment, intrusion of the environmental substance that generates the contamination substance such as the ionic impurities through voids in the lubricating layer 18 is prevented. Therefore, the amount of the contamination substance present on the surface of the magnetic recording medium 10 of the present embodiment is small. In addition, in the lubricating layer 18 in the magnetic recording medium 10 of the present embodiment, foreign matter (smear) is less likely to be generated, and pickup can be prevented. In addition, the lubricating layer 18 in the magnetic recording medium 10 of the present embodiment has excellent heat resistance and wear resistance. Therefore, the magnetic recording medium 10 of the present embodiment has excellent reliability and durability.

EXAMPLES

Hereinafter, the present invention will be more specifically described using examples and comparative examples. The present invention is not limited only to the following examples.

Example 1

A compound represented by Formula (A) shown above was produced by a method to be described below.

40 g of a compound (number-average molecular weight: 1000, molecular weight distribution: 1.1) represented by $HOCH_2CF_2O(CF_2CF_2O)_m(CF_2O)CF_2CH_2OH$ (in the formula, m is 4.5 and n is 4.5), 6.5 g of a compound (molecular weight: 272.3, 24 mmol) represented by Formula (8) shown below, and 38 mL of t-butanol (t-BuOH) were charged into a 100 ml eggplant flask under a nitrogen gas atmosphere and stirred until the mixture became uniform at room temperature. 1.4 g (molecular weight: 112.21, 12 mmol) of potassium tert-butoxide (t-BuOK) was further added to this uniform liquid and reacted by being stirred at 70° C. for 16 hours.

The compound represented by Formula (8) was synthesized by using dihydropyran to protect the hydroxyl group of glycerol α,α'-diallyl ether and then oxidizing one double bond group of the compound.

A reaction product obtained was cooled to 25° C., moved to a separatory funnel containing 100 mL of water, and extracted three times with 100 mL of ethyl acetate. The organic layer was washed with water to perform dehydration with anhydrous sodium sulfate. After the drying agent was filtered, the filtrate was concentrated, and the residue was purified by silica gel column chromatography. By performing the above steps, 20.2 g (molecular weight: 1272.3, 15.9 mmol) of the compound represented by Formula (9) shown below was obtained as an intermediate.

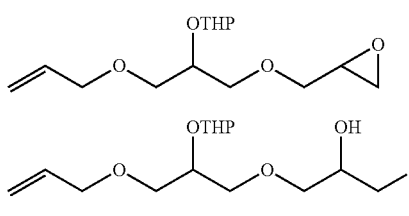

(8)

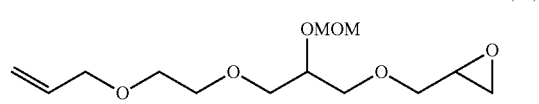

(9)

(in Formula (8), THP represents a tetrahydropyranyl group.)

(in Formula (9), m indicating the average degree of polymerization is 4.5, n indicating the average degree of polymerization is 4.5. THP represents a tetrahydropyranyl group.)

6.4 g (molecular weight: 1272.3, 5.0 mmol) of the compound represented by Formula (9) as the intermediate, 1.1 g (molecular weight: 201.3, 5.5 mmol) of a compound represented by Formula (10) shown below, and 2.4 mL of t-butanol were charged into a 100 mL eggplant flask under a nitrogen gas atmosphere and stirred until the mixture became uniform at room temperature. 1.87 g (molecular weight: 112.21, 25.2 mmol) of potassium tert-butoxide was added to this uniform liquid and reacted by being stirred at 70° C. for 22.5 hours.

The compound represented by Formula (10) was synthesized by reacting epibromohydrin with the primary hydroxyl group in 4-(3-hydroxypropyl)morpholine.

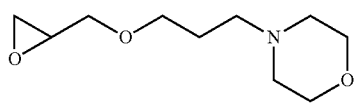

(10)

The reaction solution was returned to room temperature, and 26 g of a 10% hydrogen chloride-methanol solution (hydrogen chloride-methanol reagent (5% to 10%), manufactured by Tokyo Chemical Industry Co., Ltd.) was added thereto and stirred at room temperature for 3.5 hours. The reaction solution was moved little by little to a separatory funnel containing 100 mL of saline and extracted twice with 200 mL of ethyl acetate. The organic layer was sequentially washed with 100 mL of saline, 100 mL of saturated aqueous sodium bicarbonate, and 100 mL of saline to perform dehydration with anhydrous sodium sulfate. After the drying agent (anhydrous sodium sulfate) was filtered, the filtrate was concentrated, and the residue was purified by silica gel column chromatography. By performing the above steps, 4.6 g (3.3 mmol) of a compound (A) (in Formula (A), ma indicating the average degree of polymerization is 4.5 and na indicating the average degree of polymerization is 4.5) was obtained.

$^1$H-NMR measurement and $^{19}$F-NMR measurement of the obtained compound (A) were performed, and the structure was identified from the following results.

$^1$H-NMR (CD$_3$COCD$_3$); δ [ppm] 1.6 to 1.7 (2H), 2.4 to 2.5 (6H), 3.4 to 4.2 (30H), 5.1 to 5.2 (1H), 5.2 to 5.3 (1H), 5.8 to 5.9 (1H)

$^{19}$F-NMR (CD$_3$COCD$_3$): δ [ppm]=−55.6 to −50.6 (9F), −77.7 (2F), −80.3 (2F), −91.0 to −88.5 (18F)

Example 2

The same operation as in Example 1 was carried out except that 6.6 g of a compound represented by Formula (11) shown below was used instead of the compound represented by Formula (8), and that 1.0 g of a compound represented by Formula (12) shown below was used instead of the compound represented by Formula (10), thereby obtaining 4.7 g of a compound represented by Formula (B) shown above (in Formula (B), mb indicating the average degree of polymerization is 4.5 and nb indicating the average degree of polymerization is 4.5).

(11)

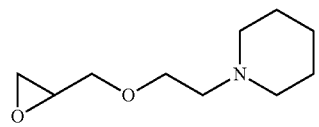

(in Formula (11), MOM represents a methoxymethyl group.)

(12)

The compound represented by Formula (11) was synthesized by a method described below. The primary hydroxyl group of ethylene glycol monoallyl ether was reacted with epibromohydrin, and the obtained compound was reacted with sulfuric acid to obtain a dialcohol. Using t-butyldimethylsilyl chloride, the primary hydroxyl group of the obtained dialcohol was protected with a t-butyldimethylsilyl group, and thereafter using methoxymethyl chloride, the secondary hydroxyl group was protected with a methoxymethyl (MOM) group. The t-butyldimethylsilyl group of the obtained compound was removed, and the resulting primary hydroxyl group was reacted with epibromohydrin. The compound represented by Formula (11) was obtained by the above-described steps.

The compound represented by Formula (12) was synthesized by reacting epibromohydrin with the primary hydroxyl group in 1-piperidine ethanol.

$^1$H-NMR measurement and $^{19}$F-NMR measurement of the obtained compound (B) were performed, and the structure was identified from the following results.

$^1$H-NMR (CD$_3$COCD$_3$); δ [ppm] 1.5 to 1.6 (6H), 2.5 to 2.8 (6H), 3.4 to 4.2 (30H), 5.1 to 5.2 (1H), 5.2 to 5.3 (1H), 5.8 to 5.9 (1H)

$^{19}$F-NMR (CD$_3$COCD$_3$): δ [ppm]=−55.6 to −50.6 (9F), −77.7 (2F), −80.3 (2F), −91.0 to −88.5 (18F)

Example 3

The same operation as in Example 1 was carried out except that 6.6 g of a compound represented by Formula (13) shown below was used instead of the compound represented by Formula (8), and that 0.9 g of a compound represented by Formula (14) shown below was used instead of the compound represented by Formula (10), thereby obtaining 4.6 g of a compound represented by Formula (C) shown above (in Formula (C), mc indicating the average degree of polymerization is 4.5 and nc indicating the average degree of polymerization is 4.5).

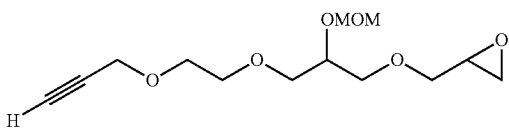

(13)

(in Formula (13), MOM represents a methoxymethyl group.)

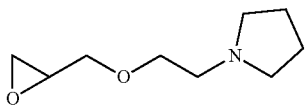

(14)

The compound represented by Formula (13) was synthesized by performing the same operation as for the compound represented by Formula (11) except that 2-(2-propynyloxy)ethanol was used instead of ethylene glycol monoallyl ether.

The compound represented by Formula (14) was synthesized by reacting epibromohydrin with the primary hydroxyl group in 1-(2-hydroxyethyl)pyrrolidine.

$^1$H-NMR measurement and $^{19}$F-NMR measurement of the obtained compound (C) were performed, and the structure was identified from the following results.

$^1$H-NMR (CD$_3$COCD$_3$); δ [ppm] 1.6 to 1.7 (4H), 2.5 to 2.8 (7H), 3.4 to 4.2 (30H)

$^{19}$F-NMR (CD$_3$COCD$_3$): δ [ppm]=−55.6 to −50.6 (9F), −77.7 (2F), −80.3 (2F), −91.0 to −88.5 (18F)

Example 4

The same operation as in Example 1 was carried out except that 6.6 g of the compound represented by Formula (11) shown above was used instead of the compound represented by Formula (8), and that 0.9 g of a compound represented by Formula (15) shown below was used instead of the compound represented by Formula (10), thereby obtaining 4.6 g of a compound represented by Formula (D) shown above (in Formula (D), md indicating the average degree of polymerization is 4.5 and nd indicating the average degree of polymerization is 4.5).

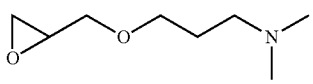

(15)

The compound represented by Formula (15) was synthesized by reacting epibromohydrin with the primary hydroxyl group in 3-(dimethylamino)-1-propanol.

$^1$H-NMR measurement and $^{19}$F-NMR measurement of the obtained compound (D) were performed, and the structure was identified from the following results.

$^1$H-NMR (CD$_3$COCD$_3$); δ [ppm] 1.7 to 1.8 (2H), 2.3 (6H), 2.5 to 2.6 (2H) 3.4 to 4.2 (32H), 5.1 to 5.2 (1H), 5.2 to 5.3 (1H), 5.8 to 5.9 (1H)

$^{19}$F-NMR (CD$_3$COCD$_3$): δ [ppm]=−55.6 to −50.6 (9F), −77.7 (2F), −80.3 (2F), −91.0 to −88.5 (18F)

Example 5

The same operation as in Example 1 was carried out except that a compound (number-average molecular weight: 1000, molecular weight distribution: 1.1) represented by HOCH$_2$CF$_2$O(CF$_2$CF$_2$O)$_{m'}$(CF$_2$O)$_{n'}$CF$_2$CH$_2$OH (in the formula, m' indicating the average degree of polymerization is 7.1, and n' indicating the average degree of polymerization is 0) was used instead of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH of Example 1 (in the formula, m indicating the average degree of polymerization is 4.5, and n indicating the average degree of polymerization is 4.5), and that 1.0 g of a compound represented by Formula (16) shown below was used instead of the compound represented by Formula (10), thereby obtaining 4.5 g of a compound represented by Formula (E) shown above (in Formula (E), me indicating the average degree of polymerization is 7.1).

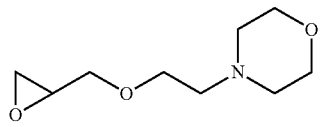

(16)

The compound represented by Formula (16) was synthesized by reacting epibromohydrin with the primary hydroxyl group in 4-(2-hydroxyethyl)morpholine.

$^1$H-NMR measurement and $^{19}$F-NMR measurement of the obtained compound (E) were performed, and the structure was identified from the following results.

$^1$H-NMR (CD$_3$COCD$_3$); δ [ppm] 2.4 to 2.5 (6H), 3.4 to 4.2 (30H), 5.1 to 5.2 (1H), 5.2 to 5.3 (1H), 5.8 to 5.9 (1H)

$^{19}$F-NMR (acetone-D$_6$): δ [ppm]=−78.6 (2F), −81.3 (2F), −90.0 to −88.5 (28F)

Example 6

The same operation as in Example 1 was carried out except that a compound (number-average molecular weight: 1000, molecular weight distribution: 1.1) represented by HOCH$_2$CF$_2$O(CF$_2$CF$_2$O)$_{m'}$(CF$_2$O)$_{n'}$CF$_2$CH$_2$OH (in the formula, m' indicating the average degree of polymerization is 7.1, and n' indicating the average degree of polymerization is 0) was used instead of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH of Example 1 (in the formula, m indicating the average degree of polymerization is 4.5, and n indicating the average degree of polymerization is 4.5), that 5.2 g of a compound represented by Formula (17) shown below was used instead of the compound represented by Formula (8), and that 1.0 g of the compound represented by Formula (16) shown above was used instead of the compound represented by Formula (10), thereby obtaining 4.6 g of a compound represented by Formula (F) shown above (in Formula (F), mf indicating the average degree of polymerization is 7.1).

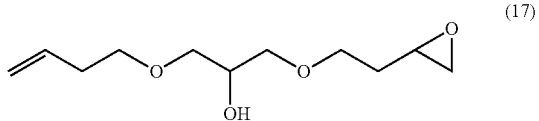

(17)

The compound represented by Formula (17) was synthesized by oxidizing one double bond group of the compound obtained by reacting 3-buten-1-ol with epichlorohydrin.

$^1$H-NMR measurement and $^{19}$F-NMR measurement of the obtained compound (F) were performed, and the structure was identified from the following results.

$^1$H-NMR (CD$_3$COCD$_3$); δ [ppm] 1.6 to 1.8 (2H), 2.3 to 2.4 (2H), 2.4 to 2.5 (6H), 3.4 to 4.2 (30H), 5.1 to 5.2 (1H), 5.2 to 5.3 (1H), 5.8 to 5.9 (1H)

$^{19}$F-NMR (acetone-D$_6$): δ [ppm]=−78.6 (2F), −81.3 (2F), −90.0 to −88.5 (28F)

Example 7

The same operation as in Example 1 was carried out except that a compound (number-average molecular weight: 1000, molecular weight distribution: 1.1) represented by HOCH$_2$CF$_2$O(CF$_2$CF$_2$O)$_{m'}$(CF$_2$O)$_{n'}$CF$_2$CH$_2$OH (in the formula, m' indicating the average degree of polymerization is 7.1, and n' indicating the average degree of polymerization is 0) was used instead of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH of Example 1 (in the formula, m indicating the average degree of polymerization is 4.5, and n indicating the average degree of polymerization is 4.5), that 5.2 g of the compound represented by Formula (17) shown above was used instead of the compound represented by Formula (8), and that 1.8 g of a compound represented by Formula (18) shown below was used instead of the compound represented by Formula (10), thereby obtaining 4.8 g of a compound represented by Formula (G) shown above (in Formula (G), mg indicating the average degree of polymerization is 7.1).

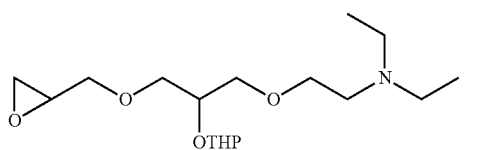

(18)

(in Formula (18), THP represents a tetrahydropyranyl group.)

The compound represented by Formula (18) was synthesized by the following method. Allyl glycidyl ether was reacted with the primary hydroxyl group in 2-diethylaminoethanol. The primary hydroxyl group in the obtained compound was protected with a tetrahydropyranyl (THP) group, and the terminal double bond of the obtained compound was oxidized. The compound represented by Formula (18) was obtained by the above-described steps.

$^1$H-NMR measurement and $^{19}$F-NMR measurement of the obtained compound (G) were performed, and the structure was identified from the following results.

$^1$H-NMR (CD$_3$COCD$_3$); δ [ppm] 1.0 (6H), 1.6 to 1.8 (2H), 2.3 to 2.4 (2H), 2.5 to 2.6 (6H), 3.4 to 4.2 (32H), 5.1 to 5.2 (1H), 5.2 to 5.3 (1H), 5.8 to 5.9 (1H)

$^{19}$F-NMR (acetone-D$_6$): δ [ppm]=−78.6 (2F), −81.3 (2F), −90.0 to −88.5 (28F)

Example 8

The same operation as in Example 1 was carried out except that a compound (number-average molecular weight: 1000, molecular weight distribution: 1.1) represented by HOCH$_2$CF$_2$O(CF$_2$CF$_2$O)$_{m'}$(CF$_2$O)$_{n'}$CF$_2$CH$_2$OH (in the formula, m' indicating the average degree of polymerization is 7.1, and n' indicating the average degree of polymerization is 0) was used instead of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH of Example 1 (in the formula, in indicating the average degree of polymerization is 4.5, and n indicating the average degree of polymerization is 4.5), that 6.2 g of a compound represented by Formula (19) shown below was used instead of the compound represented by Formula (8), and that 2.0 g of a compound represented by Formula (20) shown below was used instead of the compound represented by Formula (10), thereby obtaining 4.9 g of a compound represented by Formula (H) shown above (in Formula (H), mh indicating the average degree of polymerization is 7.1).

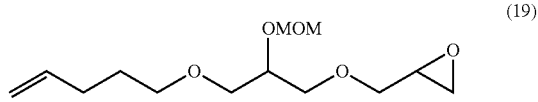

(19)

(in Formula (19), MOM represents a methoxymethyl group.)

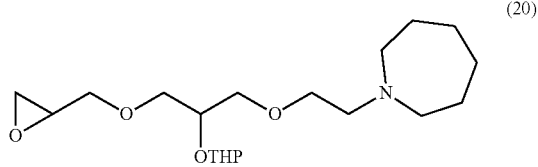

(20)

(in Formula (20), THP represents a tetrahydropyranyl group.)

The compound represented by Formula (19) was synthesized by the following method. The primary hydroxyl group of 3-(4-pentenyloxy)-1,2-propanediol was protected with a tert-butyldimethylsilyl (TBS) group, and the secondary hydroxyl group of the obtained compound was protected with a methoxymethyl (MOM) group. Thereafter, the compound, which was generated by removing the TBS group of the obtained compound, was reacted with epibromohydrin to synthesize.

The compound represented by Formula (20) was synthesized by the following method. Allyl glycidyl ether was reacted with the primary hydroxyl group in hexahydro-1H-azepine-1-ethanol. The secondary hydroxyl group in the obtained compound was protected with a THP group, and the terminal double bond of the obtained compound was oxidized. The compound represented by Formula (20) was obtained by the above-described steps.

$^1$H-NMR measurement and $^{19}$F-NMR measurement of the obtained compound (H) were performed, and the structure was identified from the following results.

$^1$H-NMR (CD$_3$COCD$_3$); δ [ppm] 1.6 to 1.8 (10H), 2.3 to 2.4 (2H), 2.4 to 2.7 (6H) 3.4 to 4.2 (32H), 5.1 to 5.2 (1H), 5.2 to 5.3 (1H), 5.8 to 5.9 (1H)

$^{19}$F-NMR (acetone-D$_6$): δ [ppm]=−78.6 (2F), −81.3 (2F), −90.0 to −88.5 (28F)

Example 9

The same operation as in Example 1 was carried out except that a compound (number-average molecular weight: 1000, molecular weight distribution: 1.1) represented by HOCH$_2$CF$_2$CF$_2$O(CF$_2$CF$_2$CF$_2$O)$_p$CF$_2$CF$_2$CH$_2$OH (in the formula, p indicating the average degree of polymerization is 4.4) was used instead of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH of Example 1 (in the formula, m indicating the average degree of polymerization is 4.5, and n indicating the average degree of polymerization is 4.5), that 6.6 g of the compound represented by Formula (13) shown above was used instead of the compound represented by Formula (8), and that 1.9 g of a compound represented by Formula (21) shown below was used instead of the compound represented by Formula (10), thereby obtaining 4.9 g of a compound represented by Formula (I) shown above (in Formula (I), pi indicating the average degree of polymerization is 4.4).

$^1$H-NMR measurement and $^{19}$F-NMR measurement of the obtained compound (I) were performed, and the structure was identified from the following results.

$^1$H-NMR (CD$_3$COCD$_3$); δ [ppm]=1.7 to 1.8 (2H), 1.8 to 1.9 (4H), 2.5 to 2.8 (7H), 3.4 to 4.2 (36H)

$^{19}$F-NMR (acetone-D$_6$): δ [ppm]=−84.0 to −83.0 (18F), −86.4 (4F), −124.3 (4F), −130.0 to −129.0 (9F)

Comparative Example 1

A compound represented by Formula (J) shown below was synthesized by the following method.

4.12 g of a compound represented by Formula (22) shown below having glycidyl groups at the molecular terminal was obtained from 4.20 g of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH (in the formula, m indicating the average degree of polymerization is 4.5, and n indicating the average degree of polymerization is 4.5) using the method disclosed in Patent Document 5.

Next, 40 mL of a dimethylamine aqueous solution (50 mass %) was added to the compound represented by Formula (22) and reacted by being stirred at room temperature for 4 hours. The organic layer was separated from the reaction product obtained after the reaction, and was dissolved in 100 mL of VERTREL (registered trademark) XF to perform dehydration with anhydrous sodium sulfate. After the drying agent was filtered, the filtrate was concentrated, thereby synthesizing 3.97 g (3.3 mmol) of a compound (J).

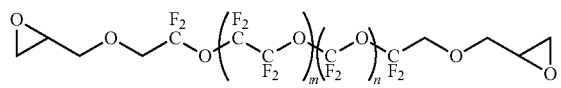

(22)

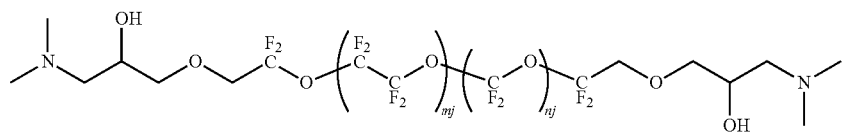

(J)

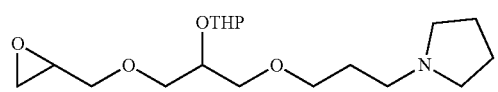

(21)

(in Formula (21), THP represents a tetrahydropyranyl group.)

The compound represented by Formula (21) was synthesized by the following method. Allyl glycidyl ether was reacted with the primary hydroxyl group in 1-(3-hydroxypropyl)pyrrolidine. The secondary hydroxyl group in the obtained compound was protected with a THP group, and the terminal double bond of the obtained compound was oxidized. The compound represented by Formula (21) was obtained by the above-described steps.

(in Formula (22), m indicating the average degree of polymerization is 4.5, and n indicating the average degree of polymerization is 4.5.)

(in Formula (J), mj indicating the average degree of polymerization is 4.5, and nj indicating the average degree of polymerization is 4.5.)

$^1$H-NMR measurement and $^{19}$F-NMR measurement of the obtained compound (J) were performed, and the structure was identified from the following results.

$^1$H-NMR (CDCl$_3$); δ [ppm]=2.3 (12H), 2.4 to 2.5 (4H), 3.4 to 4.2 (12H)

$^{19}$F-NMR (CD$_3$COCD$_3$): δ [ppm]=−55.6 to −50.6 (9F), −77.7 (2F), −80.3 (2F), −91.0 to −88.5 (18F)

Comparative Example 2

A compound represented by Formula (K) shown below was synthesized by the method disclosed in Patent Document 6.

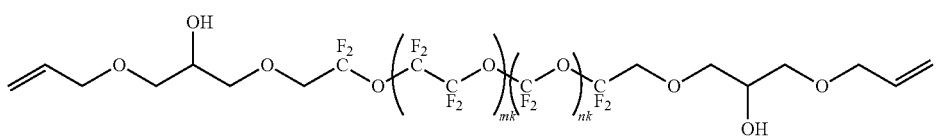

(in Formula (K), mk indicating the average degree of polymerization is 4.5, and nk indicating the average degree of polymerization is 4.5.)

$^1$H-NMR measurement and $^{19}$F-NMR measurement of the obtained compound (K) were performed, and the structure was identified from the following results.

$^1$H-NMR (CDCl$_3$); δ [ppm]=3.5 to 4.0 (20H), 5.1 to 5.3 (4H), 5.9 (2H)

$^{19}$F-NMR (CD$_3$COCD$_3$): δ [ppm]=−55.6 to −50.6 (9F), −77.7 (2F), −80.3 (2F), −91.0 to −88.5 (18F)

Comparative Example 3

A compound represented by Formula (L) shown below was synthesized by the method disclosed in Patent Document 7.

(in Formula (M), mm indicating the average degree of polymerization is 4.5, and nm indicating the average degree of polymerization is 4.5.)

$^1$H-NMR measurement of the obtained compound (M) was performed, and the structure was identified from the following results.

$^1$H-NMR (CD$_3$COCD$_3$); δ [ppm]=3.5 to 4.3 (23H), 5.1 to 5.3 (2H), 5.9 (1H), 6.2 (1H), 7.3 (1H)

Comparative Example 5

A compound represented by Formula (N) shown below was synthesized by the following method.

2.5 g of trifluoromethanesulfonic acid chloride and 0.92 g of dimethylaminopyridine were charged and stirred at −20° C. Next, 5.0 g of a compound (number-average molecular weight: 1000, molecular weight distribution: 1.1) represented by HOCH$_2$CF$_2$O(CF$_2$CF$_2$O)$_m$(CF$_2$O)$_n$CF$_2$CH$_2$OH (in the formula, m indicating the average degree of polymerization is 4.5, and n indicating the average degree of polymerization is 4.5) was added dropwise and reacted for 2 hours.

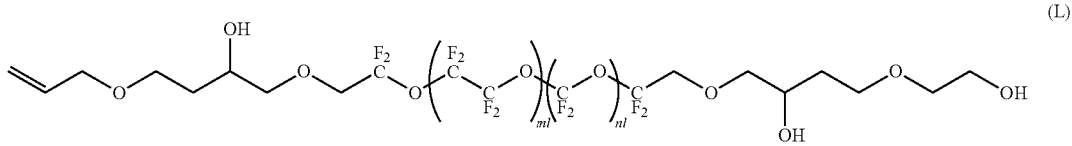

(in Formula (L), ml indicating the average degree of polymerization is 4.5, and nl indicating the average degree of polymerization is 4.5.)

$^1$H-NMR measurement and $^{19}$F-NMR measurement of the obtained compound (L) were performed, and the structure was identified from the following results.

$^1$H-NMR (CD$_3$COCD$_3$); δ [ppm]=1.6 to 1.8 (4H), 3.1 (2H), 3.5 to 4.2 (21H), 5.1 to 5.3 (2H), 5.9 (1H)

$^{19}$F-NMR (CD$_3$COCD$_3$): δ [ppm]=−55.6 to −50.6 (9F), −77.7 (2F), −80.3 (2F), −91.0 to −88.5 (18F)

Comparative Example 4

A compound represented by Formula (M) shown below was synthesized by the method disclosed in Patent Document 2.

The reaction product obtained after the reaction was returned to room temperature, moved to a separatory funnel containing 100 mL of water, and extracted three times with 100 mL of ethyl acetate. The organic layer was washed with water to perform dehydration with anhydrous sodium sulfate. After the drying agent was filtered, the filtrate was concentrated, and the residue was purified by silica gel column chromatography. By performing the above steps, 6.4

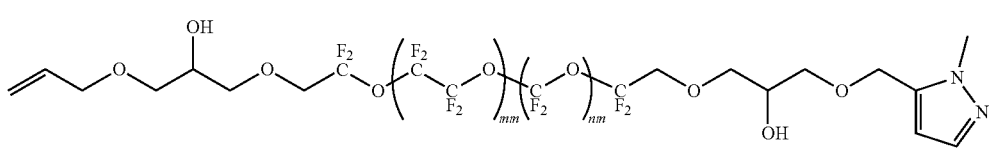

g (molecular weight: 1264, 5.1 mmol) of a compound represented by Formula (23) shown below was obtained as an intermediate.

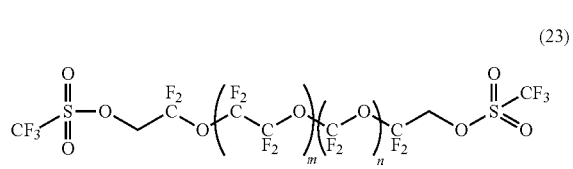

(23)

(in Formula (23), m indicating the average degree of polymerization is 4.5, and n indicating the average degree of polymerization is 4.5.)

6.0 g of the compound (molecular weight: 1264.1, 4.8 mmol) represented by Formula (23) as the intermediate, 1.8 g of a commercially available compound represented by Formula (24) shown below (manufactured by UORSY, molecular weight: 129.20, 14.2 mmol), and 12.4 mL of acetonitrile were charged into a 100 mL eggplant flask under a nitrogen gas atmosphere and stirred until the mixture became uniform at room temperature, and heating under reflux with stirring was carried out for 6 hours.

The reaction product obtained after the reaction was cooled to 25° C., moved to a separatory funnel containing 100 mL of a saturated sodium hydrogen carbonate solution, and extracted three times with 100 mL of ethyl acetate. The organic layer was washed with water to perform dehydration with anhydrous sodium sulfate. After the drying agent was filtered, the filtrate was concentrated, and the residue was purified by silica gel column chromatography. By performing the above steps, 4.0 g (3.3 mmol) of a compound (N) (in Formula (N), mn indicating the average degree of polymerization is 4.5, and nn indicating the average degree of polymerization is 4.5) was obtained.

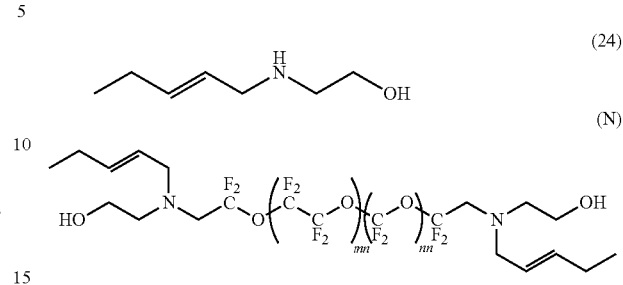

(in Formula (N), mn indicating the average degree of polymerization is 4.5, and nn indicating the average degree of polymerization is 4.5.)

$^1$H-NMR measurement of the obtained compound (N) was performed, and the structure was identified from the following results.

$^1$H-NMR (CD$_3$COCD$_3$); δ [ppm]=1.6 to 1.8 (6H), 2.3 to 2.4 (4H), 2.5 to 2.8 (12H), 3.5 to 4.1 (6H), 5.4 to 5.5 (4H)

Table 1 shows the structure of $R^1$; a, z, [X], and [Y] in Formula (3); the structure of $R^3$; the structure of $R^4$; and the structure of $R^5$ when the compounds of Examples 1 to 9 thus obtained were applied to Formula (1).

In addition, the number-average molecular weights (Mn) of the compounds of Examples 1 to 9 and Comparative Examples 1 to 5 were obtained by the above-described $^1$H-NMR and $^{19}$F-NMR measurements. Table 2 shows the results.

TABLE 1

| | $R^1$ | z | a | $R^2$ Formula (X) | Formula (Y) | $R^3$ | $R^4$ | $R^5$ | Compound |
|---|---|---|---|---|---|---|---|---|---|
| Example 1 | Allyl group | 0 | — | b = 1 c = 2 | d = 0 e = 0 | Formula (5) h = 4.5 i = 4.5 | Formula (4) f = 1 | morpholine-O-CH2CH2CH2-N | A |
| Example 2 | Allyl group | 1 | 2 | b = 1 c = 2 | d = 0 e = 0 | Formula (5) h = 4.5 i = 4.5 | Formula (4) f = 1 | piperidine-O-CH2CH2-N | B |
| Example 3 | Propargyl group | 1 | 2 | b = 1 c = 2 | d = 0 e = 0 | Formula (5) h = 4.5 i = 4.5 | Formula (4) f = 1 | pyrrolidine-O-CH2CH2-N | C |
| Example 4 | Allyl group | 1 | 2 | b = 1 c = 2 | d = 0 e = 0 | Formula (5) h = 4.5 i = 4.5 | Formula (4) f = 1 | dimethylamino-O-CH2CH2-N | D |
| Example 5 | Allyl group | 0 | — | b = 1 c = 2 | d = 0 e = 0 | Formula (5) h = 7.1 i = 0 | Formula (4) f = 1 | morpholine-O-CH2CH2-N | E |
| Example 6 | Butenyl group | 0 | — | b = 1 c = 1 | d = 2 e = 1 | Formula (5) h = 7.1 i = 0 | Formula (4) f = 1 | morpholine-O-CH2CH2-N | F |

TABLE 1-continued

| | R¹ | z | a | R² Formula (X) | Formula (Y) | R³ | R⁴ | R⁵ | Compound |
|---|---|---|---|---|---|---|---|---|---|
| Example 7 | Butenyl group | 0 | — | b = 1 c = 1 | d = 2 e = 1 | Formula (5) h = 7.1 i = 0 | Formula (4) f = 2 | ```-O~~~N(Et)₂``` | G |
| Example 8 | Pentenyl group | 0 | — | b = 1 c = 2 | d = 0 e = 0 | Formula (5) h = 7.1 i = 0 | Formula (4) f = 2 | ```-O~~~N(azepane)``` | H |
| Example 9 | Propargyl group | 1 | 2 | b = 1 c = 2 | d = 0 e = 0 | Formula (7) k = 4.4 | Formula (4) f = 2 | ```-O~~~N(pyrrolidine)``` | I |

TABLE 2

| | Film thickness (Å) | Wear resistance test | Heat resistance test Under nitrogen | Heat resistance test In atmosphere | Comprehensive evaluation | Compound | Number-average molecular weight |
|---|---|---|---|---|---|---|---|
| Example 1 | 9.0 | A | A | A | A | (A) | 1389 |
| Example 2 | 9.0 | B | A | A | A | (B) | 1418 |
| Example 3 | 9.0 | B | A | B | B | (C) | 1402 |
| Example 4 | 9.0 | B | B | B | B | (D) | 1392 |
| Example 5 | 9.0 | A | A | A | A | (E) | 1375 |
| Example 6 | 9.0 | A | A | A | A | (F) | 1404 |
| Example 7 | 9.0 | A | B | B | B | (G) | 1464 |
| Example 8 | 9.0 | B | A | B | B | (H) | 1490 |
| Example 9 | 9.0 | A | A | A | A | (I) | 1490 |
| Comparative Example 1 | 9.0 | E | B | B | D | (J) | 1202 |
| Comparative Example 2 | 9.0 | D | C | E | E | (K) | 1228 |
| Comparative Example 3 | 9.0 | C | C | E | D | (L) | 1260 |
| Comparative Example 4 | 9.0 | C | B | D | D | (M) | 1282 |
| Comparative Example 5 | 9.0 | E | B | B | D | (N) | 1224 |

Next, solutions for forming a lubricating layer were prepared using the compounds obtained in Examples 1 to 9 and Comparative Examples 1 to 5 by a method to be described below. In addition, lubricating layers of magnetic recording media were formed using the obtained solutions for forming a lubricating layer by a method to be described below, and therefore magnetic recording media of Examples 1 to 9 and Comparative Examples 1 to 5 were obtained.

"Solutions for Forming Lubricating Layer"

The compounds obtained in Examples 1 to 9 and Comparative Examples 1 to 5 were each dissolved in VERTREL (registered trademark) XF (trade name, manufactured by Dupont-Mitsui Fluorochemicals Co., Ltd.), which is a fluorine-based solvent, diluted with VERTREL XF such that the film thicknesses became 9 Å to 10 Å when applied onto protective layers, and used as solutions for forming a lubricating layer.

"Magnetic Recording Media"

Magnetic recording media each having an adhesive layer, a soft magnetic layer, a first underlayer, a second underlayer, a magnetic layer, and a protective layer sequentially provided on a substrate having a diameter of 65 mm were prepared. The protective layer was a layer made of carbon.

The solutions for forming a lubricating layer of Examples 1 to 9 and Comparative Examples 1 to 5 were each applied by the dipping method onto the protective layers of the magnetic recording media in which the individual layers up to the protective layer had been formed. The dipping method was carried out under conditions of an immersion speed of 10 mm/sec, an immersion time of 30 seconds, and a lifting speed of 1.2 mm/sec.

Thereafter, the magnetic recording media to which the solutions for forming a lubricating layer had been applied were put into a thermostatic chamber, which was maintained at 120° C., and were heated for 10 minutes to remove the solvent in the solutions for forming a lubricating layer, thereby forming lubricating layers on the protective layers and obtaining magnetic recording media.

The film thicknesses of the lubricating layers in the magnetic recording media of Examples 1 to 9 and Comparative Examples 1 to 5 obtained as described above were measured using FT-IR (trade name: Nicolet iS50, manufactured by Thermo Fisher Scientific). Table 2 shows the results.

Next, wear resistance tests were carried out as described below on the magnetic recording media of Examples 1 to 9 and Comparative Examples 1 to 5.

(Wear Resistance Test)

An alumina sphere having a diameter of 2 mm, which was a contact, was slid on the lubricating layers of the magnetic recording media using a pin-on disc-type friction wear tester at a load of 40 gf and a sliding speed of 0.25 mn/sec, and the friction coefficients of the surfaces of the lubricating layers were measured. In addition, the sliding times until the friction coefficients of the surfaces of the lubricating layers suddenly increased were measured. The sliding time until the friction coefficient suddenly increased was measured four times for the lubricating layer of each magnetic recording medium, and the average value (time) was used as an index (friction coefficient increase time) of the wear resistance of a lubricant coating film. Table 2 shows the results of the magnetic recording media for which the compounds of Examples 1 to 9 and Comparative Examples 1 to 5 were used. The friction coefficient increase times were evaluated as described below. The longer the time it takes for the friction coefficient to suddenly increase, the better the wear resistance, which is preferable.

"Evaluation Criteria"

A: 850 seconds or longer

B: equal to or longer than 750 seconds and shorter than 850 seconds

C: equal to or longer than 650 seconds and shorter than 750 seconds

D: equal to or longer than 550 seconds and shorter than 650 seconds

E: equal to or longer than 450 seconds and shorter than 550 seconds

The time until the friction coefficient suddenly increases can be used as an index of the wear resistance of the lubricating layers for the reason to be described below. The reason is that wear of the lubricating layer in the magnetic recording medium progresses from the use of the magnetic recording medium, and, once the lubricating layer is worn off due to the wear, the contact and the protective layer come into direct contact with each other, and the friction coefficient suddenly increases. The time until the friction coefficient suddenly increases is also considered to correlate with friction tests.

As shown in Table 2, wear resistance was favorable in the magnetic recording media of Examples 1 to 9 having the lubricating layers containing the compound represented by Formula (1). It is presumed that this is because the alkenyl group or alkynyl group of $R^1$ in the compounds of Examples 1 to 9 exhibits favorable interaction with the protective layers, and the tertiary amine ($—N—R^6R^7$) of $R^5$ has an appropriate bulkiness, and thereby an appropriate coating rate for the protective layers could be maintained without impairing the adhesion to the protective layers.

On the other hand, as shown in Table 2, the results of wear resistance were poor in the magnetic recording media of Comparative Examples 1 to 5 as compared to Examples 1 to 9. It is presumed that this is because the adhesion to the protective layers was difficult to obtain in the lubricating layers containing the compounds of Comparative Examples 1 to 5.

Next, the compounds of Examples 1 to 9 and Comparative Examples 1 to 5 were subjected to the following heat resistance test.

(Heat Resistance Test)

Using a thermogravimetric and differential thermal analyzer (TG-DTA) (manufactured by Bruker Corporation, product name: Galaxy), thermal decomposition measurement was performed on each of the compounds of Examples 1 to 9 and Comparative Examples 1 to 5 under nitrogen and in the atmosphere. Table 2 shows the results. The exothermic onset temperature was evaluated as follows. It is preferable as an exothermic onset temperature becomes higher because then the heat resistance is excellent.

"Evaluation Criteria"

A: 240° C. or higher

B: equal to or higher than 200° C. and lower than 240° C.

C: equal to or higher than 180° C. and lower than 200° C.

D: equal to or higher than 140° C. and lower than 180° C.

E: lower than 140° C.

As shown in Table 2, heat resistance was favorable in Examples 1 to 9 which are the compounds represented by Formula (1) because exothermic onset temperatures under nitrogen and in the atmosphere were high. It is presumed that this is because when the tertiary amine ($—N—R^6R^7$) of $R^5$ acts as a radical scavenger, this improves the heat resistance of the alkenyl group or alkynyl group of $R^1$, making oxidative decomposition due to heat less likely to occur. In addition, from the results of Examples 1 to 9, it could be confirmed that particularly excellent heat resistance can be obtained when the tertiary amine ($—N—R^6R^7$) is a morpholine group.

As shown in Table 2, in the compounds of Comparative Examples 1 and 5, there was no difference in exothermic onset temperatures between under nitrogen and in the atmosphere, showing that the level of heat resistance was almost the same as that of Examples. It is presumed that this is because the compounds of Comparative Examples 1 and 5 had a tertiary amine.

On the other hand, the results of heat resistance were poor in the compounds of Comparative Examples 2 and 3 which did not have a tertiary amine but had an alkenyl group. It is presumed that this is because the alkenyl groups were oxidatively decomposed due to heat in the compounds of Comparative Examples 2 and 3.

In addition, although Comparative Example 4 exhibited the same level of heat resistance as that of Examples under nitrogen, an exothermic onset temperature in the atmosphere was low, resulting in poor heat resistance. It is presumed that this is because the unsaturated heterocyclic ring having a nitrogen atom was decomposed due to heat, and the radical-scavenging function of the unsaturated heterocyclic ring having a nitrogen atom deteriorated.

In addition, the compounds and magnetic recording media of Examples 1 to 9 and Comparative Examples 1 to 5 were comprehensively evaluated on the basis of criteria to be described below. Table 2 shows the results.

"Evaluation Criteria"

A: evaluation of the wear resistance test was A or B, and evaluation of the heat resistance test (in the atmosphere) was A B: evaluation of the wear resistance test was A or B, and evaluation of the heat resistance test (in the atmosphere) was B C: evaluation of the wear resistance test was C, and evaluation of the heat resistance test (in the atmosphere) was A, B, or C D: evaluation of the wear resistance test was C, and evaluation of the heat resistance test (in the atmosphere) was D or E; alternatively, evaluation of the wear resistance test was D or E, and evaluation of the heat resistance test (in the atmosphere) was A, B, or C E: evaluation of the wear resistance test was D or E, and evaluation of the heat resistance test (in the atmosphere) was D or E As shown in Table 2, the comprehensive evaluation was A or B in Examples 1 to 9 in which the compound represented by Formula (1) was used. On the other hand, the comprehensive evaluation of Comparative Examples 1 and 3 to 5 was D, and the comprehensive evaluation of Comparative Example 2 was E.

INDUSTRIAL APPLICABILITY

The present invention provides a suitable fluorine-containing ether compound as a material for a lubricant for a magnetic recording medium capable of forming lubricating layers having excellent wear resistance and heat resistance.

The use of a lubricant for a magnetic recording medium containing the fluorine-containing ether compound of the present invention makes it possible to form lubricating layers that can realize excellent wear resistance and heat resistance in spite of a thin thickness.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by Formula (1) shown below, $$R^1—O—R^2—CH_2—R^3—CH_2—R^4—R^5 \quad (1)$$

(in Formula (1), $R^3$ is a perfluoropolyether chain; $R^1$ is an alkenyl group having 2 to 8 carbon atoms or an alkynyl group having 3 to 8 carbon atoms; $R^2$ and $R^4$ are each independently a divalent linking group having one or more hydroxyl groups; and —$R^5$ is a group represented by Formula (2) shown below), $$—O—(CH_2)_g—N—R^6R^7 \quad (2)$$

(in Formula (2), g is an integer of 2 or 3; $R^6$ and $R^7$ are the same or different saturated aliphatic groups; and $R^6$ and $R^7$ do not form a ring structure together with a nitrogen atom).

2. The fluorine-containing ether compound according to claim 1,
wherein —$R^2$— in Formula (1) is represented by Formula (3) shown below, $$—((CH_2)_a—O)_z—[X]—[Y]— \quad (3)$$

(in Formula (3), a represents an integer of 1 to 3, and z represents 0 or 1; [X] is represented by Formula (X) shown below, and [Y] is represented by Formula (Y) shown below, and a bonding order of [X] and [Y] may be reversed; and a sum of c in Formula (X) and e in Formula (Y) is 1 or 2),

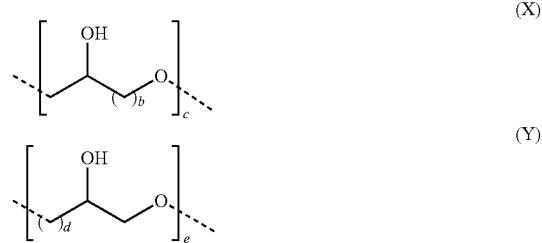

(in Formula (X), b is an integer of 1 to 3, and c is an integer of 0 to 2), and
(in Formula (Y), d is an integer of 2 or 3, and e is an integer of 0 to 2).

3. The fluorine-containing ether compound according to claim 1,
wherein —$R^4$— in Formula (1) is represented by Formula (4) shown below,

(in Formula (4), f is an integer of 1 or 2).

4. The fluorine-containing ether compound according to claim 1, wherein a total number of hydroxyl groups contained in $R^2$ and hydroxyl groups contained in $R^4$ is 3 or more.

5. The fluorine-containing ether compound according to claim 1, wherein $R^6$ and $R^7$ in Formula (2) are each independently a saturated aliphatic group having 1 to 4 carbon atoms.

6. The fluorine-containing ether compound according to claim 1, wherein —N—$R^6R^7$ in Formula (2) is a dimethylamino group or a diethylamino group.

7. The fluorine-containing ether compound according to claim 1, wherein $R^1$ in Formula (1) is any one group selected from a vinyl group, an allyl group, a 3-butenyl group, a 4-pentenyl group, and a propargyl group.

8. The fluorine-containing ether compound according to claim 1,
wherein $R^3$ is any of Formulae (5) to (7) shown below, $$—CF_2O—(CF_2CF_2O)_h—(CF_2O)_i—CF_2— \quad (5)$$

(each of h and i in Formula (5) indicates an average degree of polymerization and represents 0 to 30, provided that h and i are not both 0), $$—CF(CF_3)—(OCF(CF_3)CF_2)_j—OCF(CF_3)— \quad (6)$$

(j in Formula (6) indicates an average degree of polymerization and represents 0.1 to 30), and $$—CF_2CF_2O—(CF_2CF_2CF_2O)_k—CF_2CF_2— \quad (7)$$

(k in Formula (7) indicates an average degree of polymerization and represents 0.1 to 30).

9. The fluorine-containing ether compound according to claim 1, wherein a number-average molecular weight thereof is within a range of 500 to 10,000.

10. A fluorine-containing ether compound represented by any of Formulae (A), (B), (E), (F), and (I) shown below,

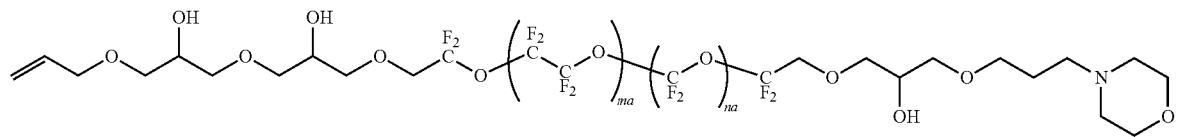
(A)

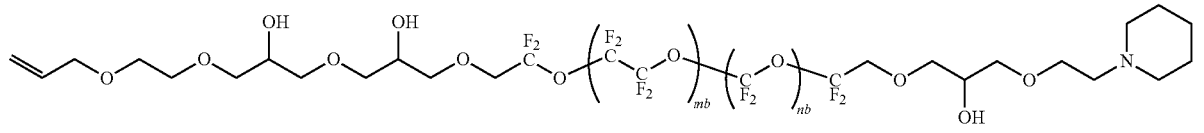
(B)

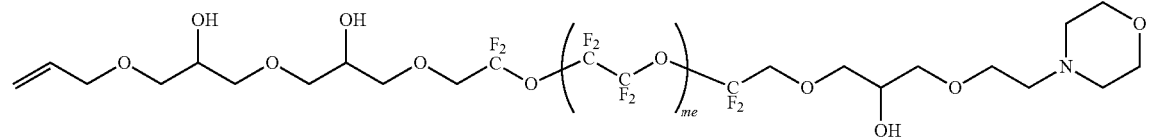
(E)

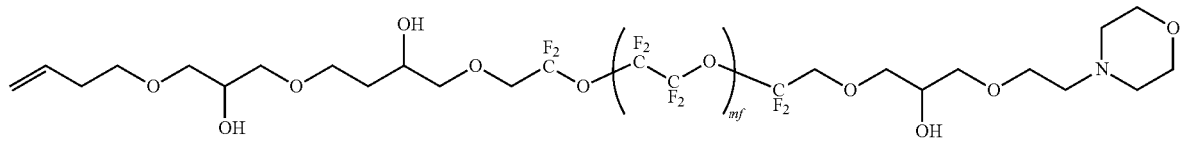
(F)

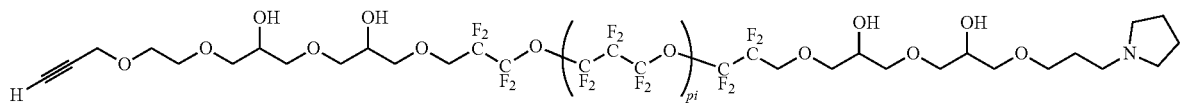
(I)

(in Formula (A), ma and na indicate average degrees of polymerization, where ma represents 1 to 30, and na represents 0 to 30), (in Formula (B), mb and nb indicate average degrees of polymerization, where mb represents 1 to 30, and nb represents 0 to 30), (in Formula (E), me indicates an average degree of polymerization, where me represents 0.1 to 30), (in Formula (F), mf indicates an average degree of polymerization, where mf represents 0.1 to 30), and (in Formula (I), pi indicates an average degree of polymerization, where pi represents 0.1 to 30).

11. A lubricant for a magnetic recording medium, wherein the lubricant comprises the fluorine-containing ether compound according to claim 1.

12. A magnetic recording medium comprising, on a substrate, at least:

a magnetic layer;

a protective layer; and a lubricating layer, in this order, wherein the lubricating layer contains the fluorine-containing ether compound according to claim 1.

13. The magnetic recording medium according to claim 12, wherein an average film thickness of the lubricating layer is 0.5 nm to 2.0 nm.

* * * * *